United States Patent
Lau et al.

(10) Patent No.: US 12,144,961 B2
(45) Date of Patent: *Nov. 19, 2024

(54) EXTENSIBLE INFUSION DEVICES AND RELATED METHODS

(71) Applicant: MEDTRONIC MINIMED, INC., Northridge, CA (US)

(72) Inventors: Belinda L. Lau, Porter Ranch, CA (US); Mirsaid Seyed-Bolorforosh, Thousand Oaks, CA (US); Desmond Barry Keenan, Valencia, CA (US)

(73) Assignee: MEDTRONIC MINIMED, INC., Northridge (CA)

( * ) Notice: Subject to any disclaimer, the term of this patent is extended or adjusted under 35 U.S.C. 154(b) by 191 days.

This patent is subject to a terminal disclaimer.

(21) Appl. No.: 17/867,232

(22) Filed: Jul. 18, 2022

(65) Prior Publication Data

US 2022/0347381 A1 Nov. 3, 2022

Related U.S. Application Data

(60) Continuation of application No. 16/389,524, filed on Apr. 19, 2019, now Pat. No. 11,406,752, which is a
(Continued)

(51) Int. Cl.
*A61M 5/142* (2006.01)
*A61M 5/172* (2006.01)
*A61M 5/158* (2006.01)

(52) U.S. Cl.
CPC ........ *A61M 5/14244* (2013.01); *A61M 5/172* (2013.01); *A61M 5/1723* (2013.01);
(Continued)

(58) Field of Classification Search
CPC ................ A61M 5/172; A61M 5/1723; A61M 5/14244; A61M 2005/14208;
(Continued)

(56) References Cited

U.S. PATENT DOCUMENTS 3,631,847 A 1/1972 Hobbs, II
4,212,738 A 7/1980 Henne
(Continued)

FOREIGN PATENT DOCUMENTS

DE 4329229 A1 3/1995
EP 0319268 A2 6/1989
(Continued)

OTHER PUBLICATIONS

Abel, P. et al., "Experience With an Implantable Glucose Sensor as a Prerequisite of an Artificial Beta Cell", Biomed Biochim Acta, 1984, vol. 43, No. 5, pp. 577-584.
(Continued)

*Primary Examiner* — Scott J Medway
*Assistant Examiner* — Anh Bui
(74) *Attorney, Agent, or Firm* — Weaver Austin Villeneuve & Sampson LLP

(57) ABSTRACT

Infusion systems, infusion devices, and related operating methods are provided. An exemplary method of operating an infusion device to deliver fluid to a user in accordance with an operating mode involves identifying a fluid type associated with the fluid currently onboard the infusion device from among a plurality of possible fluid types that is different from a previous type of fluid previously onboard the infusion device. The identified fluid type has pharmacokinetics characteristics that are different from pharmacokinetics characteristics associated with the previous fluid type. The method continues by updating one or more parameters referenced by a control module of the infusion device implementing the operating mode to reflect the pharmacokinetics characteristics associated with the identified fluid type and autonomously operating the infusion device to deliver the fluid of the identified fluid type to the user in
(Continued)

accordance with the operating mode and the one or more updated control parameters.

20 Claims, 8 Drawing Sheets

Related U.S. Application Data division of application No. 14/642,549, filed on Mar. 9, 2015, now Pat. No. 10,307,528.

(52) U.S. Cl.
CPC ............. *A61M 2005/14208* (2013.01); *A61M 2005/14296* (2013.01); *A61M 2005/1587* (2013.01); *A61M 2202/0007* (2013.01); *A61M 2205/3303* (2013.01); *A61M 2205/3306* (2013.01); *A61M 2205/332* (2013.01); *A61M 2205/3561* (2013.01); *A61M 2205/3592* (2013.01); *A61M 2205/50* (2013.01)

(58) Field of Classification Search
CPC ......... A61M 2005/14288; A61M 2005/14296; A61M 2205/50; G16H 20/10; G16H 10/60
See application file for complete search history.

(56) References Cited

U.S. PATENT DOCUMENTS

| | | |
|---|---|---|
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | DeCant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,755,173 A | 7/1988 | Konopka et al. |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,431,627 A * | 7/1995 | Pastrone ............... A61M 5/172 604/151 |
| 5,482,473 A | 1/1996 | Lord et al. |
| 5,485,408 A | 1/1996 | Blomquist |
| 5,497,772 A | 3/1996 | Schulman et al. |
| 5,505,709 A | 4/1996 | Funderburk et al. |
| 5,522,803 A | 6/1996 | Teissen-Simony |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Iliff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,807,375 A | 9/1998 | Gross et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,954,643 A | 9/1999 | Antwerp et al. |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |

(56) References Cited

U.S. PATENT DOCUMENTS

| | | | |
|---|---|---|---|
| 5,999,848 A | 12/1999 | Gord et al. |
| 5,999,849 A | 12/1999 | Gord et al. |
| 6,009,339 A | 12/1999 | Bentsen et al. |
| 6,017,328 A | 1/2000 | Fischell et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,259,937 B1 | 7/2001 | Schulman et al. |
| 6,329,161 B1 | 12/2001 | Heller et al. |
| 6,355,021 B1 | 3/2002 | Nielsen et al. |
| 6,379,301 B1 | 4/2002 | Worthington et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,485,465 B2 | 11/2002 | Moberg et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,544,212 B2 | 4/2003 | Galley et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,589,229 B1 | 7/2003 | Connelly et al. |
| 6,591,125 B1 | 7/2003 | Buse et al. |
| 6,591,876 B2 | 7/2003 | Safabash |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,736,797 B1 | 5/2004 | Larsen et al. |
| 6,740,072 B2 | 5/2004 | Starkweather et al. |
| 6,746,582 B2 | 6/2004 | Heller et al. |
| 6,747,556 B2 | 6/2004 | Medema et al. |
| 6,749,587 B2 | 6/2004 | Flaherty |
| 6,749,740 B2 | 6/2004 | Liamos et al. |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,809,653 B1 | 10/2004 | Mann et al. |
| 6,817,990 B2 | 11/2004 | Yap et al. |
| 6,827,702 B2 | 12/2004 | Lebel et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,153,263 B2 | 12/2006 | Carter et al. |
| 7,153,289 B2 | 12/2006 | Vasko |
| 7,303,549 B2 | 12/2007 | Flaherty et al. |
| 7,323,142 B2 | 1/2008 | Pendo et al. |
| 7,396,330 B2 | 7/2008 | Banet et al. |
| 7,399,277 B2 | 7/2008 | Saidara et al. |
| 7,402,153 B2 | 7/2008 | Steil et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,474,332 B2 | 7/2013 | Bente, IV |
| 8,674,288 B2 | 3/2014 | Hanson et al. |
| 9,636,453 B2 | 5/2017 | Monirabbasi et al. |
| 9,943,645 B2 | 4/2018 | Monirabbasi et al. |
| 10,105,488 B2 | 10/2018 | Palerm et al. |
| 10,307,528 B2* | 6/2019 | Lau .................. A61M 5/14244 |
| 10,307,535 B2 | 6/2019 | Palerm et al. |
| 11,406,752 B2 | 8/2022 | Lau et al. |
| 2001/0044731 A1 | 11/2001 | Coffman et al. |
| 2002/0013518 A1 | 1/2002 | West et al. |
| 2002/0055857 A1 | 5/2002 | Mault |

(56) References Cited

U.S. PATENT DOCUMENTS

| | | |
|---|---|---|
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0263354 A1 | 12/2004 | Mann et al. |
| 2005/0038331 A1 | 2/2005 | Silaski et al. |
| 2005/0038680 A1 | 2/2005 | McMahon |
| 2005/0154271 A1 | 7/2005 | Rasdal et al. |
| 2005/0192557 A1 | 9/2005 | Brauker et al. |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088521 A1 | 4/2007 | Shmueli et al. |
| 2007/0123819 A1 | 5/2007 | Mernoe et al. |
| 2007/0135866 A1 | 6/2007 | Baker et al. |
| 2008/0154503 A1 | 6/2008 | Wittenber et al. |
| 2009/0081951 A1 | 3/2009 | Erdmann et al. |
| 2009/0082635 A1 | 3/2009 | Baldus et al. |
| 2009/0281519 A1 | 11/2009 | Rao et al. |
| 2010/0160861 A1 | 6/2010 | Causey, III et al. |
| 2010/0268157 A1 | 10/2010 | Wehba et al. |
| 2012/0022443 A1 | 1/2012 | Robertson et al. |
| 2012/0190955 A1 | 7/2012 | Rao et al. |
| 2012/0191061 A1 | 7/2012 | Yodfat et al. |
| 2013/0296823 A1 | 11/2013 | Melker et al. |
| 2014/0039383 A1 | 2/2014 | Dobbles et al. |
| 2015/0051573 A1 | 2/2015 | Tieck et al. |
| 2015/0157788 A1 | 6/2015 | Gescheit et al. |
| 2015/0165117 A1 | 6/2015 | Palerm et al. |
| 2015/0217051 A1 | 8/2015 | Mastrototaro et al. |
| 2015/0217052 A1 | 8/2015 | Keenan |
| 2015/0314063 A1 | 11/2015 | Nagar et al. |
| 2016/0074536 A1 | 3/2016 | Burt |
| 2016/0158438 A1 | 6/2016 | Monirabbasi et al. |
| 2016/0158441 A1 | 6/2016 | Monirabbasi et al. |
| 2016/0175520 A1 | 6/2016 | Palerm et al. |
| 2017/0065763 A1* | 3/2017 | Rossitto ............ A61M 5/14546 |

FOREIGN PATENT DOCUMENTS

| | | |
|---|---|---|
| EP | 0806738 A1 | 11/1997 |
| EP | 0880936 A2 | 12/1998 |
| EP | 1338295 A1 | 8/2003 |
| EP | 1631036 A2 | 3/2006 |
| GB | 2218831 A | 11/1989 |
| WO | 9620745 A1 | 7/1996 |
| WO | 9636389 A1 | 11/1996 |
| WO | 9637246 A1 | 11/1996 |
| WO | 9721456 A1 | 6/1997 |
| WO | 9820439 A1 | 5/1998 |
| WO | 9824358 A2 | 6/1998 |
| WO | 9842407 A1 | 10/1998 |
| WO | 9849659 A2 | 11/1998 |
| WO | 9859487 A1 | 12/1998 |
| WO | 9908183 A1 | 2/1999 |
| WO | 9910801 A1 | 3/1999 |
| WO | 9918532 A1 | 4/1999 |
| WO | 9922236 A1 | 5/1999 |
| WO | 0010628 A2 | 3/2000 |
| WO | 0019887 A1 | 4/2000 |
| WO | 0048112 A2 | 8/2000 |
| WO | 02058537 A2 | 8/2002 |
| WO | 02066101 A2 | 8/2002 |
| WO | 03001329 A2 | 1/2003 |
| WO | 03094090 A2 | 11/2003 |
| WO | 2005065538 A2 | 7/2005 |

OTHER PUBLICATIONS

Bindra, D.S. et al., "Design and in Vitro Studies of a Needle-type Glucose Sensor for Subcutaneous Monitoring", American Chemistry Society, Sep. 1991, vol. 63, No. 17, pp. 1692-1696.

Bode, B.W. et al., "Reduction in Severe Hypoglycemia With Long-term Continuous Subcutaneous Insulin Infusion in Type I Diabetes", Diabetes Care, Apr. 1996, vol. 19, No. 4, pp. 324-327.

Boguslavsky, L. et al., "Applications of Redox Polymers in Biosensors", Solid State Ionics, Mar. 1993, vol. 60, No. 1-3, pp. 189-197.

Disetronic My Choice H-TRON plus Insulin Pump Reference Manual. no date.

Geise, R.J .et al., "Electropolymerized 1,3-Diaminobenzene for the Construction of a 1,1'-Dimethylferrocene Mediated Glucose Biosensor", Analytica Chimica Acta, Sep. 1993, vol. 281, No. 3, pp. 467-473.

Gernet, S. et al., "A Planar Glucose Enzyme Electrode", Sensors and Actuators, May 1989, vol. 17, No. 3-4, pp. 537-540.

Gernet, S. et al., "Fabrication and Characterization of a Planar Electrochemical Cell and Its Application as a Glucose Sensor", Sensors and Actuators, Jun. 1989, vol. 18, No. 1, pp. 59-70.

Gortan, L. et al., "Amperometric Glucose Sensors Based on Immobilized Glucose-Oxidizing Enymes and Chemically Modified Electrodes," Analytica Chimica Acta, 1991, vol. 249, No. 1, pp. 43-54.

Gorton, L. et al., "Amperometric Biosensors Based on an Apparent Direct Electron Transfer Between Electrodes and Immobilized Peroxiases," Analyst, Aug. 1992, vol. 117, pp. 1235-1241.

Gough, D. A. et al., "Two-Dimensional Enzyme Electrode Sensor for Glucose", Analytical Chemistry, 1985, vol. 57, No. 5, pp. 2351-2357.

Gregg, B. A. et al., "Redox Polymer Films Containing Enzymes. 1. A Redox-Conducting Epoxy Cement: Synthesis, Characterization, and Electrocatalytic Oxidation of Hydroquinone", The Journal of Physical Chemistry, 1991, vol. 95, No. 15, pp. 5970-5975.

Gregg, B.A. et al., "Cross-Linked Redox Gels Containing Glucose Oxidase for Amperometric Biosensor Applications", Analytical Chemistry, 1990, vol. 62, No. 3, pp. 258-263.

Hashiguchi, Y. et al., "Development of a Miniaturized Glucose Monitoring System by Combining a Needle-Type Glucose Sensor With Microdialysis Sampling Method," Diabetes Care, May 1994, vol. 17, No. 5, pp. 387-396.

Heller, A. et al., "Electrical Wiring of Redox Enzymes", Accounts of Chemical Research, 1990, vol. 23, No. 5, pp. 128-134.

Hirsch, I. B. et al., "Intensive Insulin Therapy for Treatment of Type I Diabetes", Diabetes Care, Dec. 1990, vol. 13, No. 12, pp. 1265-1283.

Jobst, G. et al., "Thin-Film Microbiosensors for Glucose-Lactate Monitoring",Analytical Chemistry, Sep. 15, 1996, vol. 68, No. 18, pp. 3173-3179.

Johnson, K.W. et al., "In Vivo Evaluation of an Electroenzymatic Glucose Sensor Implanted in Subcutaneous Tissue", Biosensors Bioelectronics, 1992, vol. 7, No. 10, pp. 709-714.

Jonsson, G. et al., "An Electromechanical Sensor for Hydrogen Peroxide Based on Peroxidase Adsorbed on a Spectrographic Graphite Electrode," Electroanalysis, Sep. 1989, vol. 1, No. 5, pp. 465-468.

Kanapieniene, J. J. et al., "Miniature Glucose Biosensor with Extended Linearity," Sensors and Actuators B: Chemical, Dec. 1992, vol. 10, No. 1, pp. 37-40.

(56) References Cited

OTHER PUBLICATIONS

Kawamori, R. et al., "Perfect Normalization of Excessive Glucagon Responses to Intraveneous Arginine in Human Diabetes Mellitus With the Artificial Beta-Cell", Diabetes, Sep. 1980, vol. 29, No. 9, pp. 762-765.

Kazuhiko, T. et al., "Specific Complexation with Mono- and Disaccharides that can be Detected by Circular Dichroism", J. Org. Chem., 1991, vol. 56, pp. 4089-4091.

Kimura, J. et al., "An Immobilized Enzyme Membrane Fabrication Method", Biosensors, 1988, vol. 4, No. 1, pp. 41-52.

Koudelka, M. et al., "In-vivo Behaviour of Hypodermically Implanted Microfabricated Glucose Sensors", Biosensors Bioelectronics, 1991, vol. 6, No. 1, pp. 31-36.

Koudelka, M. et al., "Planar Amperometric Enzyme-Based Glucose Microelectrode", Sensors & Actuators, Jun. 15, 1989, vol. 18, No. 2, pp. 157-165.

Mastrototaro, J.J. et al., "An Electroenzymatic Glucose Sensor Fabricated on a Flexible Substrate", Sensors and Actuators B: Chemical, Aug. 1991, vol. 5, No. 1-4, pp. 139-144.

Mastrototaro, J.J., et al., "An Electroenzymatic Sensor Capable of 72 Hour Continuous Monitoring of Subcutaneous Glucose", 14th Annual International Diabetes Federation Congress, Washington D.C., Jun. 1991, pp. 23-28.

McKean, B. D. et al., "A Telemetry-Instrumentation System for Chronically Implanted Glucose and Oxygen Sensors", IEEE Transactions on Biomedical Engineering, Jul. 1988, vol. 35, No. 7, pp. 526-532.

Monroe, D., "Novel Implantable: Glucose Sensors", ACL, Dec. 1989, pp. 8-16.

Morff, R.J., et al., "Microfabrication of Reproducible, Economical, Electroenzymatic Glucose Sensors", Annual International Conference of the IEEE Engineering in Medicine and Biology Society, 1990, vol. 12, No. 2, pp. 483-484.

Moussy, F. et al., "Performance of Subcutaneously Implanted Needle-Type Glucose Sensors Employing a Novel Trilayer Coating," Analytical Chemistry, Aug. 1, 1993, vol. 65, No. 15, pp. 2072-2077.

Nakamoto, S. et al., "A Lift-Off Method for Patterning Enzyme-Immobilized Membranes in Multi-Biosensors", Sensors and Actuators, Feb. 1988, vol. 13, No. 2, pp. 165-172.

Nishida, K. et al., "Clinical Applications of the Wearable Artificel Endocrine Pancreas with the Newly Designed Needle-Type Glucose Sensor," Elsevier Sciences B.V., 1994, pp. 353-358.

Nishida, K. et al., "Development of a Ferrocene-mediated Needle-type Glucose Sensor Covered With Newly Designed Biocompatible Membrane, 2-methacryloyloxyethylphosphorylcholine-co-n-butyl Methacrylate", Medical Progress Through Technology, 1995, vol. 21, No. 2, pp. 91-103.

PCT Search Report PCT/US2002/003299, dated Oct. 31, 2002, Medtronic Minimed, Inc.

Poitout, V. et al., "A Glucose Monitoring System for on Line Estimation in Man of Blood Glucose Concentration Using a Miniaturized Glucose Sensor Implanted in the Subcutaneous Tissue and a Wearable Control Unit", Diabetologia, Jul. 1993, vol. 36, No. 7, pp. 658-663.

Reach, G. et al., "A Method for Evaluating in vivo the Functional Characteristics of Glucose Sensors", Biosensors, 1986, vol. 2, No. 4, pp. 211-220.

Shaw, G. W. et al., "In Vitro Testing of a Simply Constructed, Highly Stable Glucose Sensor Suitable for Implantation in Diabetic Patients", Biosensors and Bioelectronics, 1991, vol. 6, No. 5, pp. 401-406.

Shichiri, M., "A Needle-Type Glucose Sensor—A Valuable Tool Not Only for a Self-Blood Glucose Monitoring but for a Wearable Artifiical Pancreas", Life Support Systems Proceedings, XI Annual Meeting ESAO, Alpbach-Innsbruck, Austria, Sep. 1984, pp. 7-9.

Shichiri, M. et al., "An Artificial Endocrine Pancreas-problems Awaiting Solution for Long-term Clinical Applications of a Glucose Sensor", Frontiers of Medical and Biological Engineering : the International Journal of the Japan Society of Medical Electronics and Biological Engineering, 1991, vol. 3, No. 4, pp. 283-292.

Shichiri, M. et al., "Closed-loop Glycemic Control With a Wearable Artificial Endocrine Pancreas. Variations in Daily Insulin Requirements to Glycemic Response", Diabetes, Dec. 1984, vol. 33, No. 12, pp. 1200-1202.

Shichiri, M. et al., "Glycaemic Control in Pancreatectomized Dogs With a Wearable Artificial Endocrine Pancreas", Diabetologia, Mar. 1983, vol. 24, No. 3, pp. 179-184.

Shichiri, M. et al., "In Vivo Characteristics of Needle-type Glucose Sensor-measurements of Subcutaneous Glucose Concentrations in Human Volunteers", Hormone and Metabolic Research. Supplement Series, 1988, vol. 20, pp. 17-20.

Shichiri, M. et al., "Membrane Design for Extending the Long-Life of an Implantable Glucose Sensor,"Diabetes Nutrition and Metabolism, 1989, vol. 2, No. 4, pp. 309-313.

Shichiri, M. et al., "Normalization of the Paradoxic Secretion of Glucagon in Diabetics Who Were Controlled by the Artificial Beta Cell", Diabetes, Apr. 1979, vol. 28, No. 4, pp. 272-275.

Shichiri, M. et al., "Telemetry Glucose Monitoring Device With Needle-type Glucose Sensor: a Useful Tool for Blood Glucose Monitoring in Diabetic Individuals", Diabetes care, May-Jun. 1986, vol. 9, No. 3, pp. 298-301.

Shichiri, M. et al., "The Wearable Artificial Endocrine Pancreas with a Needle-Type Glucose Sensor: Perfect Glycemic Control in Ambulatory Diabetes," Acta Paediatrica Japonica, 1984, vol. 26, No. 3, pp. 359-370.

Shichiri, M. et al., "Wearable Artificial Endocrine Pancrease With Needle-type Glucose Sensor", Lancet, Nov. 1982, vol. 2, No. 8308, pp. 1129-1131.

Shults, M. C., "A Telemetry-Instrumentation System for Monitoring Multiple Subcutaneously Implanted Glucose Sensors", IEEE Transactions on Bio-medical Engineering, Oct. 1994, vol. 41, No. 10, pp. 937-942.

Sternberg, R. et al., "Study and Development of Multilayer Needle-type Enzyme-based Glucose Microsensors", Biosensors, 1989, vol. 4, pp. 27-40.

Strowig, S. M., "Initiation and Management of Insulin Pump Therapy", The Diabetes Educator, Feb. 1993, vol. 19, No. 1, pp. 50-60.

Tamiya, E. et al., "Micro Glucose Sensors using Electron Mediators Immobilized on a Polypyrrole-Modified Electrode", Sensors and Actuators, 1989, vol. 18, pp. 297-307.

Urban, G., et al., "Miniaturized Multi-enzyme Biosensors Integrated With Ph Sensors on Flexible Polymer Carriers for in Vivo Applications", Biosensors Bioelectronics, 1992, vol. 7, pp. 733-739.

Urban, G., et al., "Miniaturized Thin-film Biosensors Using Covalently Immobilized Glucose Oxidase", Biosensors Bioelectronics, 1991, vol. 6, pp. 555-562.

U.S. Non-Final Office Action dated Aug. 27, 2018, in U.S. Appl. No. 14/642,549.

U.S. Non-Final Office Action dated Dec. 7, 2021, in U.S. Appl. No. 16/389,524.

U.S. Non-Final Office Action dated Sep. 28, 2017, in U.S. Appl. No. 14/642,549.

U.S. Notice of Allowance dated Apr. 6, 2022 in U.S. Appl. No. 16/389,524.

U.S. Notice of Allowance dated Jan. 23, 2019, in U.S. Appl. No. 14/642,549.

U.S. Restriction requirement dated May 10, 2017, in U.S. Appl. No. 14/642,549.

Velho, G., et al., "In Vivo Calibration of a Subcutaneous Glucose Sensor for Determination of Subcutaneous Glucose Kinetics", Diab. Nutr. Metab., 1988, vol. 3, pp. 227-233.

Wang, J. et al., "Needle-type Dual Microsensor for the Simultaneous Monitoring of Glucose and Insulin", Analytical Chemistry, Feb. 15, 2001, vol. 73, No. 4, pp. 844-847.

Yamasaki, Y. et al.,"Direct Measurement of Whole Blood Glucose by a Needle-type Sensor", Clinica Chimica Acta; International Journal of Clinical Chemistry, Mar. 15, 1989, vol. 180, No. 1, pp. 93-98.

Yokoyama, K. et al., "Integrated Biosensor for Glucose and Galactose", Analytica Chimica Acta, 1989, vol. 218, pp. 137-142.

\* cited by examiner

EXTENSIBLE INFUSION DEVICES AND RELATED METHODS

CROSS-REFERENCE TO RELATED APPLICATIONS

This application is a continuation of U.S. patent application Ser. No. 16/389,524, filed Apr. 19, 2019, which is a division of U.S. patent application Ser. No. 14/642,549, filed Mar. 9, 2015.

TECHNICAL FIELD

Embodiments of the subject matter described herein relate generally to medical devices, and more particularly, embodiments of the subject matter relate to fluid infusion devices accommodating multiple different infused fluids with common operating modes.

BACKGROUND

Infusion pump devices and systems are relatively well known in the medical arts, for use in delivering or dispensing an agent, such as insulin or another prescribed medication, to a patient. A typical infusion pump includes a pump drive system which typically includes a small motor and drive train components that convert rotational motor motion to a translational displacement of a plunger (or stopper) in a reservoir that delivers medication from the reservoir to the body of a user via a fluid path created between the reservoir and the body of a user. Use of infusion pump therapy has been increasing, especially for delivering insulin for diabetics.

Continuous insulin infusion provides greater control of a diabetic's condition, and hence, control schemes are being developed that allow insulin infusion pumps to monitor and regulate a user's blood glucose level in a substantially continuous and autonomous manner. For example, an insulin infusion pump may operate in a closed-loop operating mode overnight while a user is sleeping to regulate the user's glucose level to a target glucose level. In practice, multiple different operating modes for providing continuous insulin infusion may be supported by an infusion pump, however, care must be taken when transitioning between operating modes to avoid potentially compromising a user's condition and ensure compliance with applicable regulatory requirements.

Infusion pumps have been traditionally designed and configured with a particular drug and physiological condition in mind. However, as different drugs enter or exit the market, or different physiological conditions are capable of being regulated via fluid infusion, it is desirable to accommodate future infusion scenarios as seamlessly as possible while maintaining compliance with applicable regulatory requirements.

BRIEF SUMMARY

Infusion devices, systems and related methods of operation are provided. One exemplary method of operating an infusion device to deliver fluid to a user in accordance with an operating mode involves identifying a fluid type associated with the fluid currently onboard the infusion device from among a plurality of possible fluid types that is different from a previous type of fluid previously onboard the infusion device. The identified fluid type has pharmacokinetics characteristics that are different from pharmacokinetics characteristics associated with the previous fluid type. The method continues by updating one or more parameters referenced by a control module of the infusion device implementing the operating mode to reflect the pharmacokinetics characteristics associated with the identified fluid type and autonomously operating the infusion device to deliver the fluid of the identified fluid type to the user in accordance with the operating mode and the one or more updated control parameters.

In another embodiment, a method of operating an infusion device in accordance with an operating mode involves autonomously operating the infusion device to deliver a first fluid to a user in accordance with the operating mode and first values for one or more parameters of the operating mode referenced by a control module of the infusion device implementing the operating mode, where the first values are associated with a first fluid type of the first fluid. Thereafter, the method identifies a second fluid type associated with a second fluid onboard the infusion device that has pharmacokinetics characteristics different from the first fluid type. In response to identifying the second fluid type, the method automatically updates the one or more parameters referenced by the control module to second values associated with the second fluid type of the second fluid that reflect the pharmacokinetics characteristics associated with the second fluid type, and after updating the one or more parameters, autonomously operating the infusion device to deliver the second fluid to the user in accordance with the operating mode and the second values for the one or more parameters.

An embodiment of an infusion device is also provided. The infusion device includes a data storage element to maintain initial values for control parameters of an operating mode, a motor operable to deliver fluid influencing a physiological condition to a body of a user, and a control system coupled to the motor and the data storage element. The control system operates the motor to deliver the fluid to the user in accordance with the operating mode using the initial values for the control parameters of the operating mode. Thereafter, the control system identifies a different fluid type associated with the fluid currently onboard the infusion device having pharmacokinetics characteristics different from a previous fluid type onboard the infusion device from among a plurality of possible fluid types. In response to identifying the different fluid type, the control system updates control parameter values maintained by the data storage element to updated values that are different from the initial values and reflect the pharmacokinetics characteristics of the identified fluid type, and thereafter, the control system operates the motor to deliver the fluid to the user in accordance with the operating mode using the updated values for the control parameters of the operating mode.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

DETAILED DESCRIPTION

Figure 1:
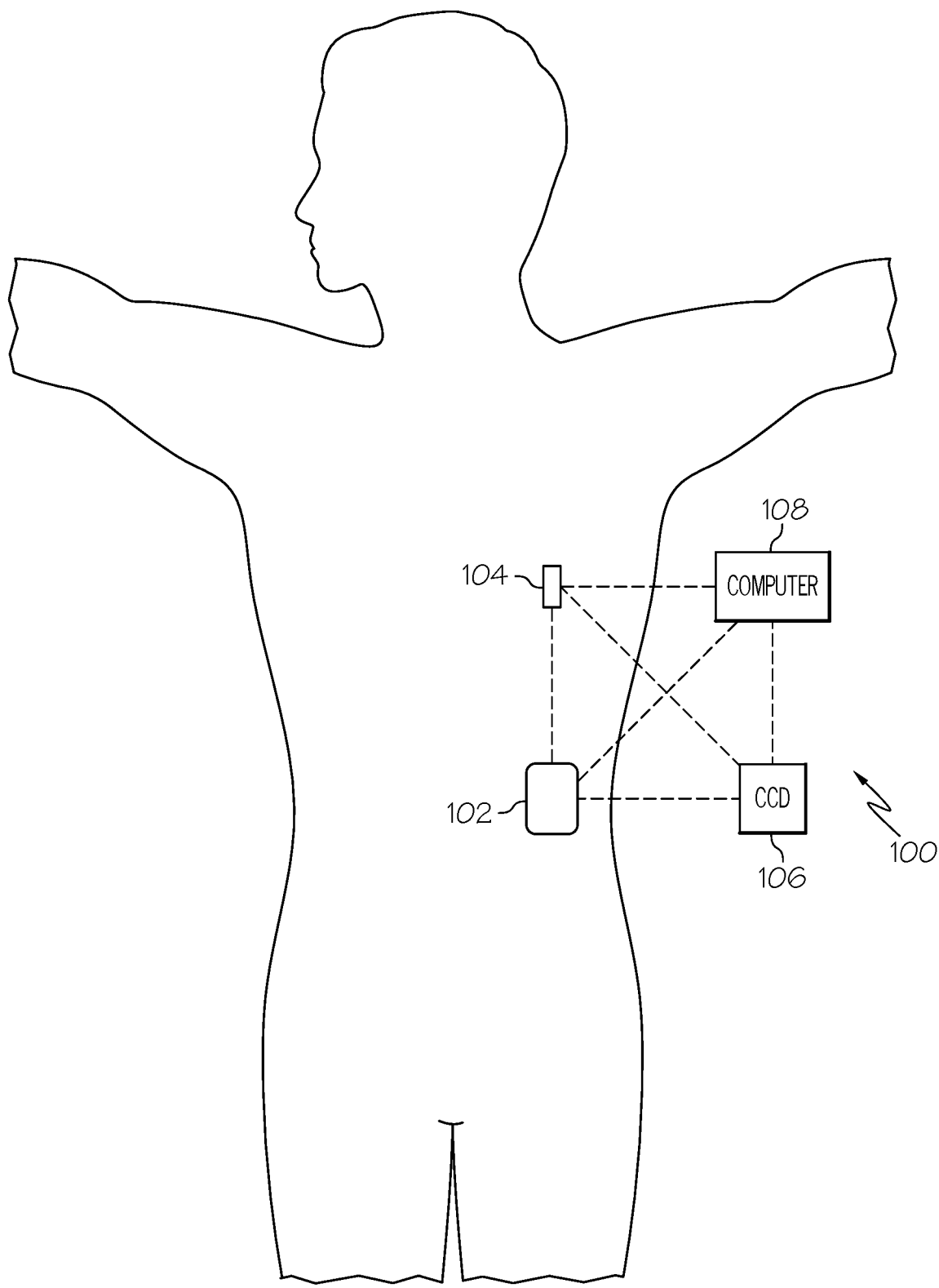
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

While the subject matter described herein can be implemented in any electronic device that includes a motor, exemplary embodiments described below are implemented in the form of medical devices, such as portable electronic medical devices. Although many different applications are possible, the following description focuses on a fluid infusion device (or infusion pump) as part of an infusion system deployment. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Embodiments of the subject matter described herein generally relate to fluid infusion devices including a motor that is operable to linearly displace a plunger (or stopper) of a reservoir provided within the fluid infusion device to deliver a dosage of fluid, such as insulin, to the body of a user. Dosage commands that govern operation of the motor may be generated in an automated and autonomous manner in accordance with the delivery control scheme associated with a particular operating mode. For example, in a closed-loop operating mode, the dosage commands are generated based on a difference between a current (or most recent) measurement of a physiological condition in the body of the user (e.g., an interstitial fluid glucose level) and a target (or reference) value for that physiological condition. In a predictive operating mode, the dosage commands may be influenced by a predicted value (or anticipated measurement) for that physiological condition in the body of the user at some point in the future. Conversely, in an open-loop operating mode, the dosage commands may be configured to implement a predetermined delivery rate substantially independent of the current or predicted measurements of the physiological condition of the user.

As described in greater detail below in the context of FIGS. 6-9, in exemplary embodiments, the delivery control scheme associated with a particular operating mode utilized to determine dosage commands governing operation of the motor is implemented in a manner that is extensible or adaptable to accommodate different types of infused fluid (e.g., different drugs or medications) having different pharmacokinetics characteristics using the same common control scheme architecture or algorithms. In response to identifying a change in the fluid type onboard the infusion device, values for the parameters referenced by the infusion device control module when implementing delivery control scheme are automatically updated to reflect the different pharmacokinetics characteristics associated with the new fluid type onboard the infusion device. Thereafter, the infusion device control module resumes autonomous operation of the infusion device by generating dosage commands using the same delivery control scheme that was utilized for the previous fluid type but with the updated parameter values that reflect the different pharmacokinetics characteristics associated with the currently onboard fluid type. In addition to updating values for pharmacokinetics control parameters that are dictated by or otherwise correlative to the drug pharmacokinetics characteristics, values for patient-specific control parameters utilized by the operating mode are also automatically updated, either to reflect user settings previously specified for use with the current drug or to otherwise adapt user settings specified for use with the previous drug in a manner that accounts for the change in pharmacokinetics characteristics when using the current drug.

Turning now to FIG. 1, one exemplary embodiment of an infusion system 100 includes, without limitation, a fluid infusion device (or infusion pump) 102, a sensing arrangement 104, a command control device (CCD) 106, and a computer 108. The components of an infusion system 100 may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. Pat. No. 8,674,288, the subject matter of which is hereby incorporated by reference in its entirety.

In the illustrated embodiment of FIG. 1, the infusion device 102 is designed as a portable medical device suitable for infusing a fluid, a liquid, a gel, or other agent into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 104 generally represents the components of the infusion system 100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 104 may include electronics and enzymes reactive to a biological condition, such as a blood glucose level, or the like, of the user, and provide data indicative of the blood glucose level to the infusion device 102, the CCD 106 and/or the computer 108. For example, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108.

Still referring to FIG. 1, in various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106 and/or the computer 108. In such embodiments, the sensing arrangement 104 may be configured to receive a biological sample, analyte, or the like, to measure a condition of the user.

As described above, in some embodiments, the CCD 106 and/or the computer 108 may include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the user that facilitates the user's subsequent use of the infusion device 102. For example, the CCD 106 may provide information to the user to allow the user to determine the rate or dose of medication to be administered into the patient's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be used for determining glucose levels in the blood and/or body fluids of the user without the use of, or necessity of, a wire or cable connection between the infusion device 102 and the sensing arrangement 104 and/or the CCD 106.

In some embodiments, the sensing arrangement 104 and/or the infusion device 102 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, 7,323,142, and 7,402,153, all of which are incorporated herein by reference in their entirety. In such embodiments, the sensing arrangement 104 is configured to sense or measure a condition of the user, such as, blood glucose level or the like. The infusion device 102 is configured to deliver fluid in response to the condition sensed by the sensing arrangement 104. In turn, the sensing arrangement 104 continues to sense or otherwise quantify a current condition of the user, thereby allowing the infusion device 102 to deliver fluid substantially continuously in response to the condition currently (or most recently) sensed by the sensing arrangement 104 indefinitely. In some embodiments, the sensing arrangement 104 and/or the infusion device 102 may be configured to utilize the closed-loop system only for a portion of the day, for example, only when the user is asleep or awake.

Figure 2:
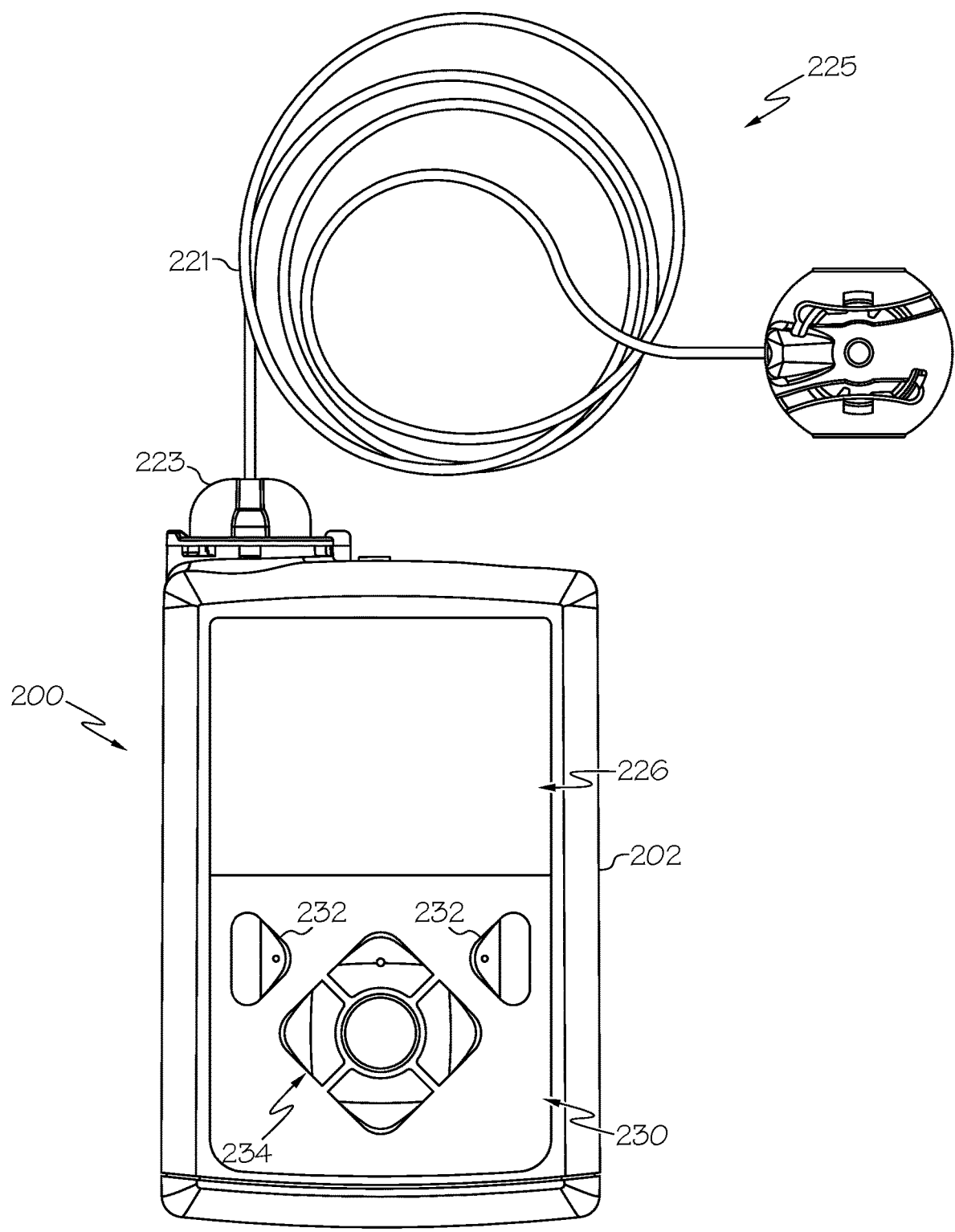
FIG. 2 depicts a plan view of an exemplary embodiment of a fluid infusion device suitable for use in the infusion system of FIG. 1.
Figure 3:
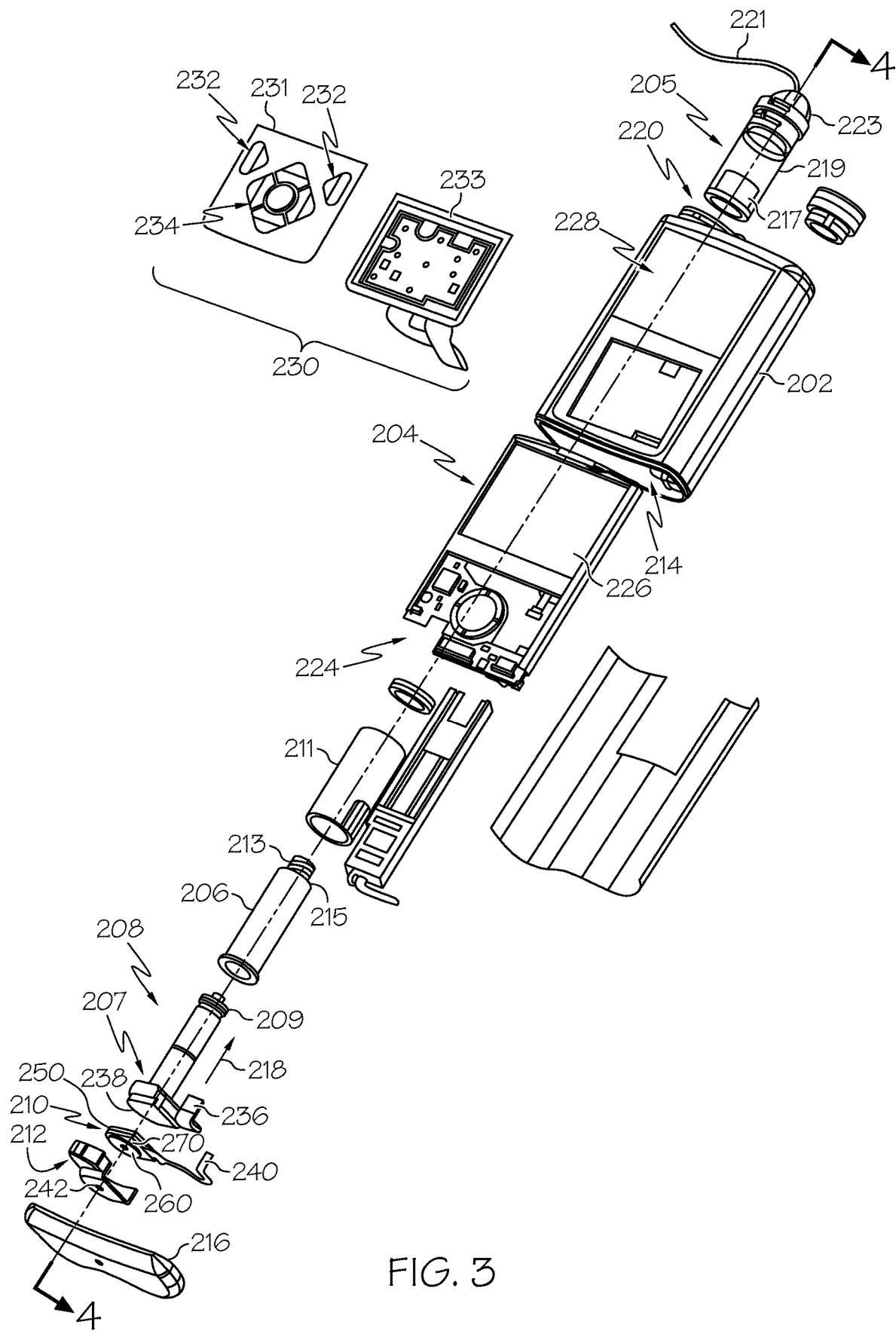
FIG. 3 is an exploded perspective view of the fluid infusion device of FIG. 2.
Figure 4:
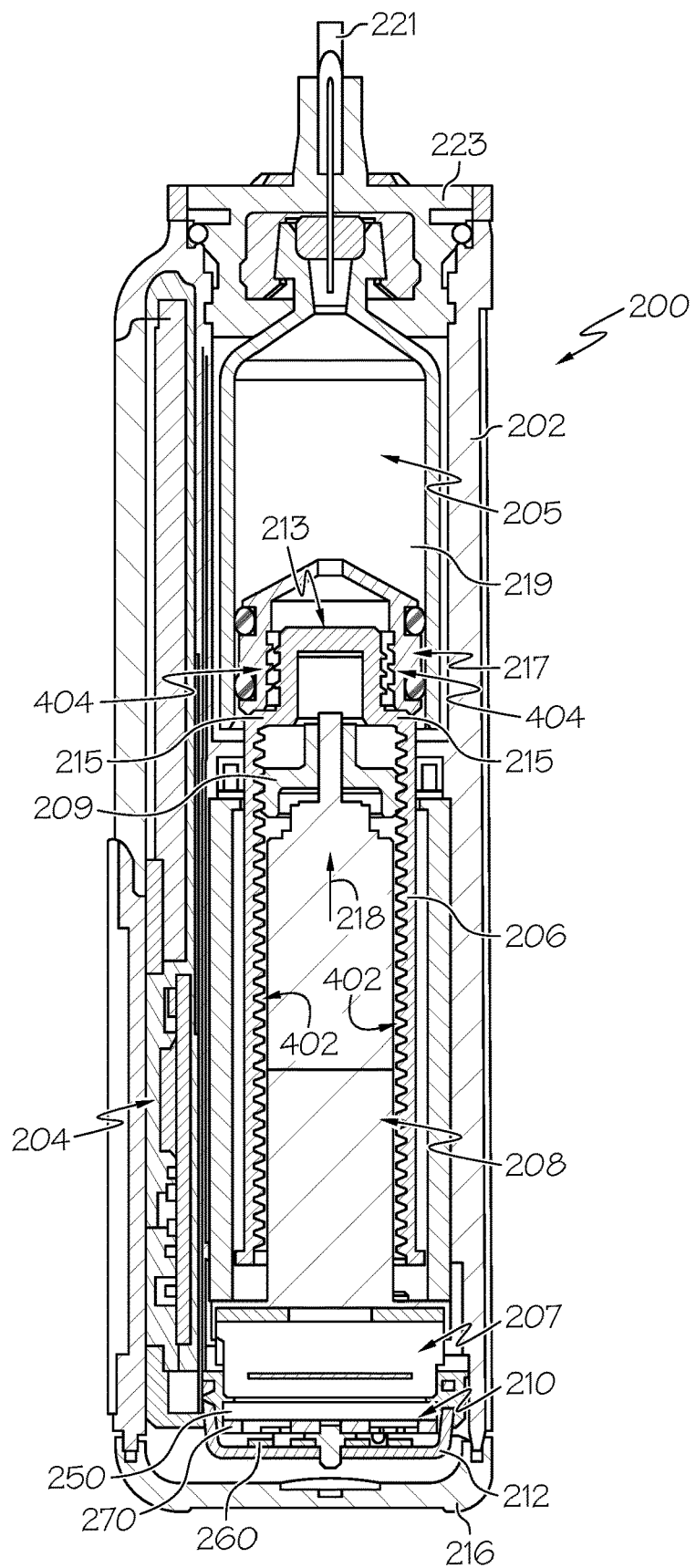
FIG. 4 is a cross-sectional view of the fluid infusion device of FIGS. 2-3 as viewed along line 4-4 in FIG. 3 when assembled with a reservoir inserted in the infusion device.

FIGS. 2-4 depict one exemplary embodiment of a fluid infusion device 200 (or alternatively, infusion pump) suitable for use in an infusion system, such as, for example, as infusion device 102 in the infusion system 100 of FIG. 1. The fluid infusion device 200 is a portable medical device designed to be carried or worn by a patient (or user), and the fluid infusion device 200 may leverage any number of conventional features, components, elements, and characteristics of existing fluid infusion devices, such as, for example, some of the features, components, elements, and/or characteristics described in U.S. Pat. Nos. 6,485,465 and 7,621,893. It should be appreciated that FIGS. 2-4 depict some aspects of the infusion device 200 in a simplified manner; in practice, the infusion device 200 could include additional elements, features, or components that are not shown or described in detail herein.

As best illustrated in FIGS. 2-3, the illustrated embodiment of the fluid infusion device 200 includes a housing 202 adapted to receive a fluid-containing reservoir 205. An opening 220 in the housing 202 accommodates a fitting 223 (or cap) for the reservoir 205, with the fitting 223 being configured to mate or otherwise interface with tubing 221 of an infusion set 225 that provides a fluid path to/from the body of the user. In this manner, fluid communication from the interior of the reservoir 205 to the user is established via the tubing 221. The illustrated fluid infusion device 200 includes a human-machine interface (HMI) 230 (or user interface) that includes elements 232, 234 that can be manipulated by the user to administer a bolus of fluid (e.g., insulin), to change therapy settings, to change user preferences, to select display features, and the like. The infusion device also includes a display element 226, such as a liquid crystal display (LCD) or another suitable display element, that can be used to present various types of information or data to the user, such as, without limitation: the current glucose level of the patient; the time; a graph or chart of the patient's glucose level versus time; device status indicators; etc.

The housing 202 is formed from a substantially rigid material having a hollow interior 214 adapted to allow an electronics assembly 204, a sliding member (or slide) 206, a drive system 208, a sensor assembly 210, and a drive system capping member 212 to be disposed therein in addition to the reservoir 205, with the contents of the housing 202 being enclosed by a housing capping member 216. The opening 220, the slide 206, and the drive system 208 are coaxially aligned in an axial direction (indicated by arrow 218), whereby the drive system 208 facilitates linear displacement of the slide 206 in the axial direction 218 to dispense fluid from the reservoir 205 (after the reservoir 205 has been inserted into opening 220), with the sensor assembly 210 being configured to measure axial forces (e.g., forces aligned with the axial direction 218) exerted on the sensor assembly 210 responsive to operating the drive system 208 to displace the slide 206. In various embodiments, the sensor assembly 210 may be utilized to detect one or more of the following: an occlusion in a fluid path that slows, prevents, or otherwise degrades fluid delivery from the reservoir 205 to a patient's body; when the reservoir 205 is empty; when the slide 206 is properly seated with the reservoir 205; when a fluid dose has been delivered; when the infusion pump 200 is subjected to shock or vibration; when the infusion pump 200 requires maintenance.

Depending on the embodiment, the fluid-containing reservoir 205 may be realized as a syringe, a vial, a cartridge, a bag, or the like. In certain embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. As best illustrated in FIGS. 3-4, the reservoir 205 typically includes a reservoir barrel 219 that contains the fluid and is concentrically and/or coaxially aligned with the slide 206 (e.g., in the axial direction 218) when the reservoir 205 is inserted into the infusion pump 200. The end of the reservoir 205 proximate the opening 220 may include or otherwise mate with the fitting 223, which secures the reservoir 205 in the housing 202 and prevents displacement of the reservoir 205 in the axial direction 218 with respect to the housing 202 after the reservoir 205 is inserted into the housing 202. As described above, the fitting 223 extends from (or through) the opening 220 of the housing 202 and mates with tubing 221 to establish fluid communication from the interior of the reservoir 205 (e.g., reservoir barrel 219) to the user via the tubing 221 and infusion set 225. The opposing end of the reservoir 205 proximate the slide 206 includes a plunger 217 (or stopper) positioned to push fluid from inside the barrel 219 of the reservoir 205 along a fluid path through tubing 221 to a user. The slide 206 is configured to mechanically couple or otherwise engage with the plunger 217, thereby becoming seated with the plunger 217 and/or reservoir 205. Fluid is forced from the reservoir 205 via tubing 221 as the drive system 208 is operated to displace the slide 206 in the axial direction 218 toward the opening 220 in the housing 202.

In the illustrated embodiment of FIGS. 3-4, the drive system 208 includes a motor assembly 207 and a drive screw 209. The motor assembly 207 includes a motor that is coupled to drive train components of the drive system 208 that are configured to convert rotational motor motion to a translational displacement of the slide 206 in the axial direction 218, and thereby engaging and displacing the plunger 217 of the reservoir 205 in the axial direction 218. In some embodiments, the motor assembly 207 may also be powered to translate the slide 206 in the opposing direction (e.g., the direction opposite direction 218) to retract and/or detach from the reservoir 205 to allow the reservoir 205 to be replaced. In exemplary embodiments, the motor assembly 207 includes a brushless DC (BLDC) motor having one or more permanent magnets mounted, affixed, or otherwise disposed on its rotor. However, the subject matter described herein is not necessarily limited to use with BLDC motors, and in alternative embodiments, the motor may be realized as a solenoid motor, an AC motor, a stepper motor, a piezoelectric caterpillar drive, a shape memory actuator drive, an electrochemical gas cell, a thermally driven gas cell, a bimetallic actuator, or the like. The drive train components may comprise one or more lead screws, cams, ratchets, jacks, pulleys, pawls, clamps, gears, nuts, slides, bearings, levers, beams, stoppers, plungers, sliders, brackets, guides, bearings, supports, bellows, caps, diaphragms, bags, heaters, or the like. In this regard, although the illustrated embodiment of the infusion pump utilizes a coaxially aligned drive train, the motor could be arranged in an offset or otherwise non-coaxial manner, relative to the longitudinal axis of the reservoir 205.

As best shown in FIG. 4, the drive screw 209 mates with threads 402 internal to the slide 206. When the motor assembly 207 is powered and operated, the drive screw 209 rotates, and the slide 206 is forced to translate in the axial direction 218. In an exemplary embodiment, the infusion pump 200 includes a sleeve 211 to prevent the slide 206 from rotating when the drive screw 209 of the drive system 208 rotates. Thus, rotation of the drive screw 209 causes the slide 206 to extend or retract relative to the drive motor assembly 207. When the fluid infusion device is assembled and operational, the slide 206 contacts the plunger 217 to engage the reservoir 205 and control delivery of fluid from the infusion pump 200. In an exemplary embodiment, the shoulder portion 215 of the slide 206 contacts or otherwise engages the plunger 217 to displace the plunger 217 in the axial direction 218. In alternative embodiments, the slide 206 may include a threaded tip 213 capable of being detachably engaged with internal threads 404 on the plunger 217 of the reservoir 205, as described in detail in U.S. Pat. Nos. 6,248,093 and 6,485,465, which are incorporated by reference herein.

As illustrated in FIG. 3, the electronics assembly 204 includes control electronics 224 coupled to the display element 226, with the housing 202 including a transparent window portion 228 that is aligned with the display element 226 to allow the display 226 to be viewed by the user when the electronics assembly 204 is disposed within the interior 214 of the housing 202. The control electronics 224 generally represent the hardware, firmware, processing logic and/or software (or combinations thereof) configured to control operation of the motor assembly 207 and/or drive system 208, as described in greater detail below in the context of FIG. 5. Whether such functionality is implemented as hardware, firmware, a state machine, or software depends upon the particular application and design constraints imposed on the embodiment. Those familiar with the concepts described here may implement such functionality in a suitable manner for each particular application, but such implementation decisions should not be interpreted as being restrictive or limiting. In an exemplary embodiment, the control electronics 224 includes one or more programmable controllers that may be programmed to control operation of the infusion pump 200.

The motor assembly 207 includes one or more electrical leads 236 adapted to be electrically coupled to the electronics assembly 204 to establish communication between the control electronics 224 and the motor assembly 207. In response to command signals from the control electronics 224 that operate a motor driver (e.g., a power converter) to regulate the amount of power supplied to the motor from a power supply, the motor actuates the drive train components of the drive system 208 to displace the slide 206 in the axial direction 218 to force fluid from the reservoir 205 along a fluid path (including tubing 221 and an infusion set), thereby administering doses of the fluid contained in the reservoir 205 into the patient's body. Preferably, the power supply is realized one or more batteries contained within the housing 202. Alternatively, the power supply may be a solar panel, capacitor, AC or DC power supplied through a power cord, or the like. In some embodiments, the control electronics 224 may operate the motor of the motor assembly 207 and/or drive system 208 in a stepwise manner, typically on an intermittent basis; to administer discrete precise doses of the fluid to the user according to programmed delivery profiles.

Referring to FIGS. 2-4, as described above, the user interface 230 includes HMI elements, such as buttons 232 and a directional pad 234, that are formed on a graphic keypad overlay 231 that overlies a keypad assembly 233, which includes features corresponding to the buttons 232, directional pad 234 or other user interface items indicated by the graphic keypad overlay 231. When assembled, the keypad assembly 233 is coupled to the control electronics 224, thereby allowing the HMI elements 232, 234 to be manipulated by the user to interact with the control electronics 224 and control operation of the infusion pump 200, for example, to administer a bolus of insulin, to change therapy settings, to change user preferences, to select display features, to set or disable alarms and reminders, and the like. In this regard, the control electronics 224 maintains and/or provides information to the display 226 regarding program parameters, delivery profiles, pump operation, alarms, warnings, statuses, or the like, which may be adjusted using the HMI elements 232, 234. In various embodiments, the HMI elements 232, 234 may be realized as physical objects (e.g., buttons, knobs, joysticks, and the like) or virtual objects (e.g., using touch-sensing and/or proximity-sensing technologies). For example, in some embodiments, the display 226 may be realized as a touch screen or touch-sensitive display, and in such embodiments, the features and/or functionality of the HMI elements 232, 234 may be integrated into the display 226 and the HMI 230 may not be present. In some embodiments, the electronics assembly 204 may also include alert generating elements coupled to the control electronics 224 and suitably configured to generate one or more types of feedback, such as, without limitation: audible feedback; visual feedback; haptic (physical) feedback; or the like.

Referring to FIGS. 3-4, in accordance with one or more embodiments, the sensor assembly 210 includes a back plate structure 250 and a loading element 260. The loading element 260 is disposed between the capping member 212 and a beam structure 270 that includes one or more beams having sensing elements disposed thereon that are influenced by compressive force applied to the sensor assembly 210 that deflects the one or more beams, as described in greater detail in U.S. Pat. No. 8,474,332, which is incorporated by reference herein. In exemplary embodiments, the back plate structure 250 is affixed, adhered, mounted, or otherwise mechanically coupled to the bottom surface 238 of the drive system 208 such that the back plate structure 250 resides between the bottom surface 238 of the drive system 208 and the housing cap 216. The drive system capping member 212 is contoured to accommodate and conform to the bottom of the sensor assembly 210 and the drive system 208. The drive system capping member 212 may be affixed to the interior of the housing 202 to prevent displacement of the sensor assembly 210 in the direction opposite the direction of force provided by the drive system 208 (e.g., the direction opposite direction 218). Thus, the sensor assembly 210 is positioned between the motor assembly 207 and secured by the capping member 212, which prevents displacement of the sensor assembly 210 in a downward direction opposite the direction of arrow 218, such that the sensor assembly 210 is subjected to a reactionary compressive force when the drive system 208 and/or motor assembly 207 is operated to displace the slide 206 in the axial direction 218 in opposition to the fluid pressure in the reservoir 205. Under normal operating conditions, the compressive force applied to the sensor assembly 210 is correlated with the fluid pressure in the reservoir 205. As shown, electrical leads 240 are adapted to electrically couple the sensing elements of the sensor assembly 210 to the electronics assembly 204 to establish communication to the control electronics 224, wherein the control electronics 224 are configured to measure, receive, or otherwise obtain electrical signals from the sensing elements of the sensor assembly 210 that are indicative of the force applied by the drive system 208 in the axial direction 218.

Figure 5:
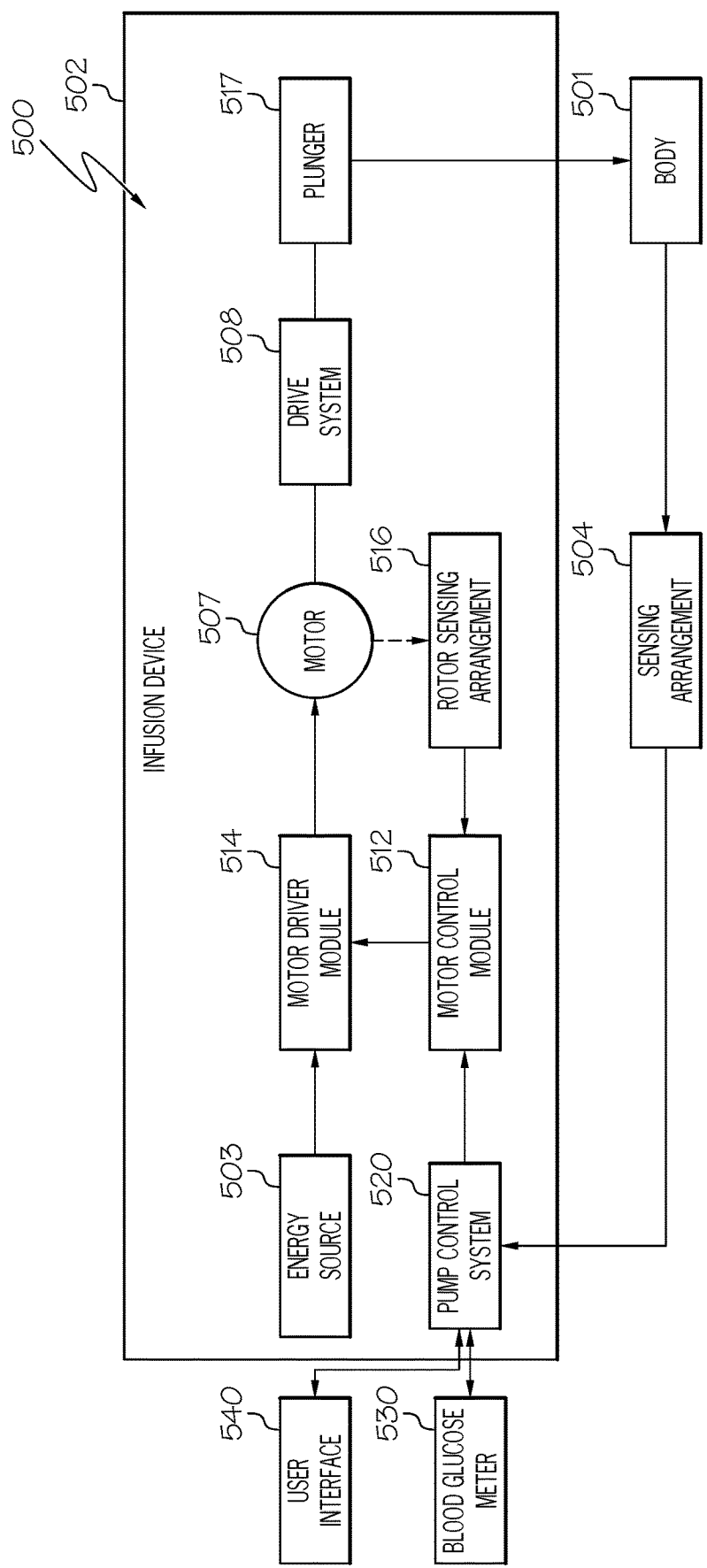
FIG. 5 is a block diagram of an exemplary control system suitable for use in a fluid infusion device, such as the fluid infusion device of FIG. 1 or FIG. 2.

FIG. 5 depicts an exemplary embodiment of a control system 500 suitable for use with an infusion device 502, such as the infusion device 102 in FIG. 1 or the infusion device 200 of FIG. 2. The control system 500 is configured to control or otherwise regulate a physiological condition in the body 501 of a user. In one or more exemplary embodiments, the condition being regulated is sensed, detected, measured or otherwise quantified by a sensing arrangement 504 (e.g., sensing arrangement 104) communicatively coupled to the infusion device 502. However, it should be noted that in alternative embodiments, the condition being regulated by the control system 500 may be correlative to the measured values obtained by the sensing arrangement 504. That said, for clarity and purposes of explanation, the subject matter may be described herein in the context of the sensing arrangement 504 being realized as a glucose sensing arrangement that senses, detects, measures or otherwise quantifies the user's glucose level, which is being regulated in the body 501 of the user by the control system 500.

In exemplary embodiments, the sensing arrangement 504 includes one or more interstitial glucose sensing elements that generate or otherwise output electrical signals having a signal characteristic that is correlative to, influenced by, or otherwise indicative of the relative interstitial fluid glucose level in the body 501 of the user. The output electrical signals are filtered or otherwise processed to obtain a measurement value indicative of the user's interstitial fluid glucose level. In exemplary embodiments, a blood glucose meter 530, such as a finger stick device, is utilized to directly sense, detect, measure or otherwise quantify the blood glucose in the body 501 of the user. In this regard, the blood glucose meter 530 outputs or otherwise provides a measured blood glucose value that may be utilized as a reference measurement for calibrating the sensing arrangement 504 and converting a measurement value indicative of the user's interstitial fluid glucose level into a corresponding calibrated blood glucose measurement value. For purposes of explanation, sensor glucose value, sensed glucose value, glucose measurement value, or variants thereof should be understood to encompass any glucose value indicative of a current measured glucose level in the body of the user that is based on the electrical signals output by the sensing element(s) of the sensing arrangement 504.

The pump control system 520 generally represents the electronics and other components of the infusion device 502 that control operation of the fluid infusion device 502 according to a desired infusion delivery program in a manner that may be influenced by the sensed glucose value indicative of a current glucose level in the body 501 of the user. The particular operating mode being implemented by the pump control system 520 influences the generated dosage commands for operating the motor 507 to displace the plunger 517 and deliver insulin to the body 501 of the user. For example, in a closed-loop (CL) operating mode, the pump control system 520 generates or otherwise determines dosage commands for operating the motor 507 based on the difference between a sensed glucose value and the target (or commanded) glucose value to regulate the sensed glucose value to the target. In other operating modes, the pump control system 520 may generate or otherwise determine dosage commands configured to maintain the sensed glucose value below an upper glucose limit, above a lower glucose limit, or otherwise within a desired range of glucose values. For example, in a predictive low glucose management (PLGM) operating mode, the pump control system 520 calculates or otherwise determines a predicted glucose value based on the currently sensed glucose value, and generates dosage commands configured to provide a basal infusion rate when the predicted glucose value is greater than a predictive suspend threshold and automatically suspends delivery (e.g., by providing dosage commands equal to zero) when the predicted glucose value is less than the predictive suspend threshold. In a low glucose suspend (LGS) operating mode, the pump control system 520 generates dosage commands configured to provide a basal infusion rate when the sensed glucose value is greater than a suspend threshold (which may be different from the predictive suspend threshold) and automatically suspends delivery when the sensed glucose value is less than the suspend threshold. In an open-loop (OL) operating mode, the pump control system 520 generates dosage commands configured to provide a predetermined open-loop basal infusion rate independent of the sensed glucose value. In practice, the infusion device 502 may store or otherwise maintain the target value, suspension threshold values, and/or other glucose threshold value(s) in a data storage element accessible to the pump control system 520.

The target glucose value and other threshold values may be received from an external component (e.g., CCD 106 and/or computing device 108) or be input by a user via a user interface element 540 associated with the infusion device 502. In practice, the one or more user interface element(s) 540 associated with the infusion device 502 typically include at least one input user interface element, such as, for example, a button, a keypad, a keyboard, a knob, a joystick, a mouse, a touch panel, a touchscreen, a microphone or another audio input device, and/or the like. Additionally, the one or more user interface element(s) 540 include at least one output user interface element, such as, for example, a display element (e.g., a light-emitting diode or the like), a display device (e.g., a liquid crystal display or the like), a speaker or another audio output device, a haptic feedback device, or the like, for providing notifications or other information to the user. It should be noted that although FIG. 5 depicts the user interface element(s) 540 as being separate from the infusion device 502, in practice, one or more of the user interface element(s) 540 may be integrated with the infusion device 502. Furthermore, in some embodiments, one or more user interface element(s) 540 are integrated with the sensing arrangement 504 in addition to and/or in alternative to the user interface element(s) 540 integrated with the infusion device 502. The user interface element(s) 540 may be manipulated by the user to operate the infusion device 502 to deliver correction boluses, adjust target and/or threshold values, modify the delivery control scheme or operating mode, and the like, as desired.

In exemplary embodiments, the pump control system 520 includes or otherwise accesses a data storage element, memory, or other non-transitory computer-readable medium capable of storing programming instructions for execution by the pump control system 520. The computer-executable programming instructions, when read and executed, cause the pump control system 520 to determine dosage commands in accordance with a particular operating mode and perform various additional tasks, operations, functions, and processes described herein.

Still referring to FIG. 5, in the illustrated embodiment, the infusion device 502 includes a motor control module 512 coupled to a motor 507 (e.g., motor assembly 207) that is operable to displace a plunger 517 (e.g., plunger 217) in a reservoir (e.g., reservoir 205) and provide a desired amount of fluid to the body 501 of a user. In this regard, displacement of the plunger 517 results in the delivery of a fluid that is capable of influencing the condition in the body 501 of the user to the body 501 of the user via a fluid delivery path (e.g., via tubing 221 of an infusion set 225). A motor driver module 514 is coupled between an energy source 503 and the motor 507. The motor control module 512 is coupled to the motor driver module 514, and the motor control module 512 generates or otherwise provides command signals that operate the motor driver module 514 to provide current (or power) from the energy source 503 to the motor 507 to displace the plunger 517 in response to receiving, from a pump control system 520, a dosage command indicative of the desired amount of fluid to be delivered.

In exemplary embodiments, the energy source 503 is realized as a battery housed within the infusion device 502 (e.g., within housing 202) that provides direct current (DC) power. In this regard, the motor driver module 514 generally represents the combination of circuitry, hardware and/or other electrical components configured to convert or otherwise transfer DC power provided by the energy source 503 into alternating electrical signals applied to respective phases of the stator windings of the motor 507 that result in current flowing through the stator windings that generates a stator magnetic field and causes the rotor of the motor 507 to rotate.

The motor control module 512 is configured to receive or otherwise obtain a commanded dosage from the pump control system 520, convert the commanded dosage to a commanded translational displacement of the plunger 517, and command, signal, or otherwise operate the motor driver module 514 to cause the rotor of the motor 507 to rotate by an amount that produces the commanded translational displacement of the plunger 517. For example, the motor control module 512 may determine an amount of rotation of the rotor required to produce translational displacement of the plunger 517 that achieves the commanded dosage received from the pump control system 520. Based on the current rotational position (or orientation) of the rotor with respect to the stator that is indicated by the output of the rotor sensing arrangement 516, the motor control module 512 determines the appropriate sequence of alternating electrical signals to be applied to the respective phases of the stator windings that should rotate the rotor by the determined amount of rotation from its current position (or orientation). In embodiments where the motor 507 is realized as a BLDC motor, the alternating electrical signals commutate the respective phases of the stator windings at the appropriate orientation of the rotor magnetic poles with respect to the stator and in the appropriate order to provide a rotating stator magnetic field that rotates the rotor in the desired direction. Thereafter, the motor control module 512 operates the motor driver module 514 to apply the determined alternating electrical signals (e.g., the command signals) to the stator windings of the motor 507 to achieve the desired delivery of fluid to the user.

When the motor control module 512 is operating the motor driver module 514, current flows from the energy source 503 through the stator windings of the motor 507 to produce a stator magnetic field that interacts with the rotor magnetic field. In some embodiments, after the motor control module 512 operates the motor driver module 514 and/or motor 507 to achieve the commanded dosage, the motor control module 512 ceases operating the motor driver module 514 and/or motor 507 until a subsequent dosage command is received. In this regard, the motor driver module 514 and the motor 507 enter an idle state during which the motor driver module 514 effectively disconnects or isolates the stator windings of the motor 507 from the energy source 503. In other words, current does not flow from the energy source 503 through the stator windings of the motor 507 when the motor 507 is idle, and thus, the motor 507 does not consume power from the energy source 503 in the idle state, thereby improving efficiency.

Depending on the embodiment, the motor control module 512 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. Furthermore, the steps of a method or algorithm described in connection with the embodiments disclosed herein may be embodied directly in hardware, in firmware, in a software module executed by the motor control module 512, or in any practical combination thereof. In exemplary embodiments, the motor control module 512 includes or otherwise accesses a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the motor control module 512. The computer-executable programming instructions, when read and executed by the motor control module 512, cause the motor control module 512 to perform the tasks, operations, functions, and processes described herein.

It should be appreciated that FIG. 5 is a simplified representation of the infusion device 502 for purposes of explanation and is not intended to limit the subject matter described herein in any way. In this regard, depending on the embodiment, some features and/or functionality of the sensing arrangement 504 may be implemented by or otherwise integrated into the pump control system 520, or vice versa. Similarly, in practice, the features and/or functionality of the motor control module 512 may be implemented by or otherwise integrated into the pump control system 520, or vice versa. Furthermore, the features and/or functionality of the pump control system 520 may be implemented by control electronics 224 located in the fluid infusion device 200, while in alternative embodiments, the pump control system 520 may be implemented by a remote computing device that is physically distinct and/or separate from the infusion device 502, such as, for example, the CCD 106 or the computing device 108.

Figure 6:
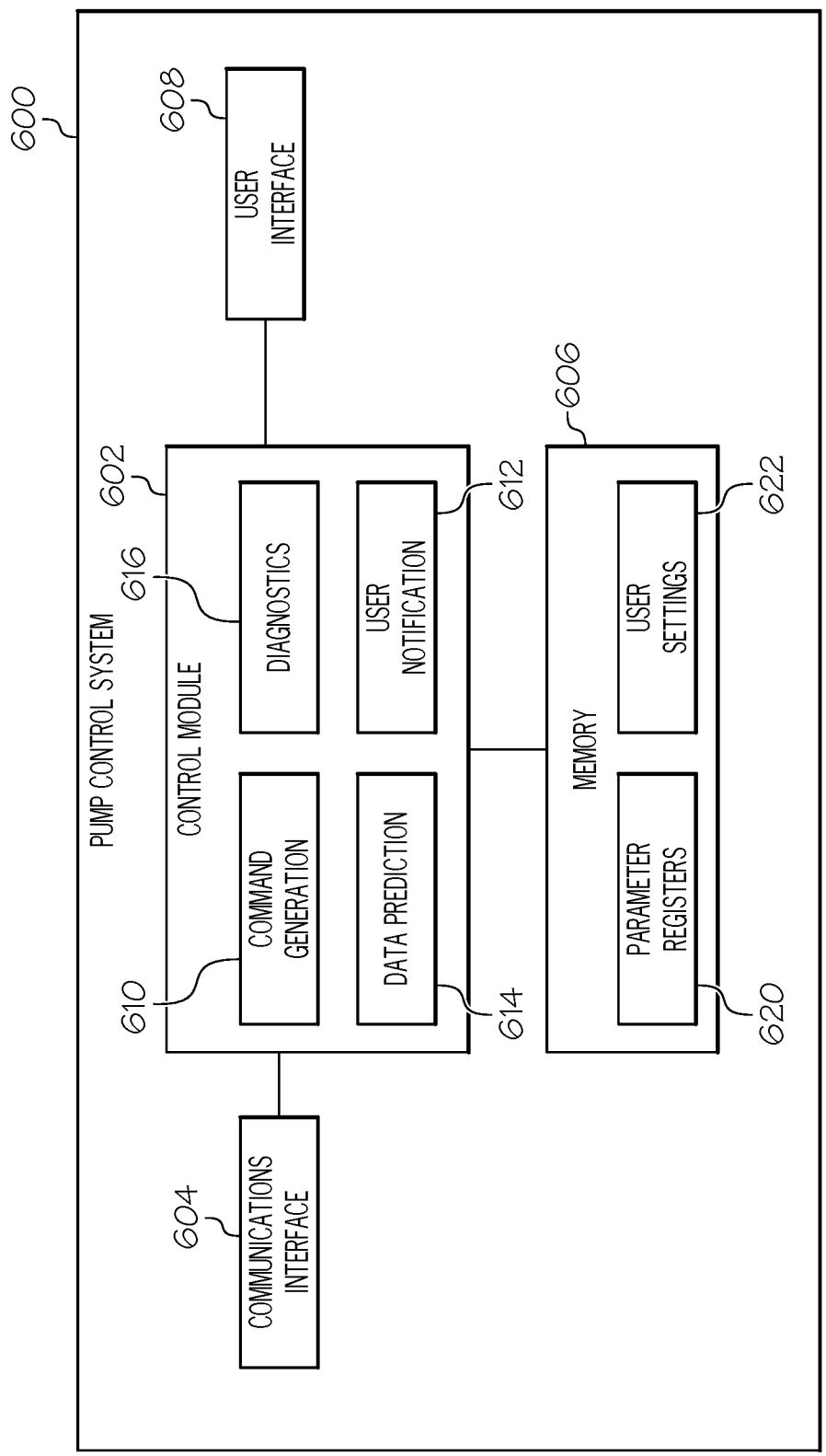
FIG. 6 is a block diagram of an exemplary pump control system suitable for use in the control system of FIG. 5.

FIG. 6 depicts an exemplary embodiment of a pump control system 600 suitable for use as the pump control system 520 in FIG. 5 in accordance with one or more embodiments. The illustrated pump control system 600 includes, without limitation, a pump control module 602, a communications interface 604, and a data storage element (or memory) 606. The pump control module 602 is coupled to the communications interface 604 and the memory 606, and the pump control module 602 is suitably configured to support the operations, tasks, and/or processes described herein. In exemplary embodiments, the pump control module 602 is also coupled to one or more user interface elements 608 (e.g., user interface 230, 540) for receiving user inputs (e.g., user preferences or settings, bolus or other delivery instructions, and the like) and providing notifications or other information to the user. Although FIG. 6 depicts the user interface element 608 as being integrated with the pump control system 600 (e.g., as part of the infusion device 200, 502), in various alternative embodiments, the user interface element 608 may be integrated with the sensing arrangement 504 or another element of an infusion system 100 (e.g., the computer 108 or CCD 106).

Referring to FIG. 6 and with reference to FIG. 5, the communications interface 604 generally represents the hardware, circuitry, logic, firmware and/or other components of the pump control system 600 that are coupled to the pump control module 602 and configured to support communications between the pump control system 600 and the sensing arrangement 504. In this regard, the communications interface 604 may include or otherwise be coupled to one or more transceiver modules capable of supporting wireless communications between the pump control system 520, 600 and the sensing arrangement 504 or another electronic device 106, 108 in an infusion system 100. In other embodiments, the communications interface 604 may be configured to support wired communications to/from the sensing arrangement 504. The communications interface 604 may also include or otherwise be coupled to one or more transceiver modules configured to support communications between the pump control module 602 and a communications network including additional devices external to the infusion system 100, such as, the internet, a wireless local area network (WLAN), or the like.

The pump control module 602 generally represents the hardware, circuitry, logic, firmware and/or other component (s) of the pump control system 600 that is configured to determine dosage commands for operating the motor 507 to deliver fluid to the body 501 based on measurement data received from the sensing arrangement 504 and perform various additional tasks, operations, functions and/or operations described herein. Depending on the embodiment, the pump control module 602 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the pump control module 602, or in any practical combination thereof.

In exemplary embodiments, the pump control module 602 includes or otherwise accesses the data storage element or memory 606, which may be realized using any sort of non-transitory computer-readable medium capable of storing programming instructions for execution by the pump control module 602. The computer-executable programming instructions, when read and executed by the pump control module 602, cause the pump control module 602 to perform the tasks, operations, functions, and processes described herein. In this regard, a control scheme or algorithm implemented by the pump control module 602 may be realized as control application code that is stored or otherwise maintained in the memory 606 and executed by the pump control module 602 to implement or otherwise provide one or more of the components in software. For example, the control application code may be executed by the control module 602 to obtain a command generation application 610 that implements or otherwise provides one or more of the closed-loop PID control components of the closed-loop control system 700 described in greater detail below in the context of FIG. 7. The command generation application 610 automatically calculates or otherwise determines a dosage command for operating the motor 507 of the infusion device 502 in accordance with a delivery control scheme of a particular operating mode based at least in part on a current measurement value for a condition in the body 501 of the user (e.g., the current sensor glucose measurement value received from the sensing arrangement 504) and one or more pharmacokinetic control parameters for the operating mode stored in corresponding parameter registers 620 in memory 606. In some embodiments described herein, the command generation application 610 supports multiple different operating modes having different delivery control schemes associated therewith. Additionally, the command generation application 610 may generate dosage commands for delivering boluses that are manually-initiated or otherwise instructed by a user via a user interface element 608.

The illustrated pump control module 602 also implements or otherwise executes a notification application 612 that generates or otherwise provides user notifications or alerts via a user interface element 608 based at least in part on a current measurement value for the condition in the body 501 of the user. For example, the notification application 612 may access patient-specific notification criteria associated with the current operating mode implemented by the command generation application 610 and automatically generate user notifications in a manner that is influenced by the sensor glucose measurement values received from the sensing arrangement 504 and/or the dosage commands generated by the command generation application 610. Various implementation details pertaining to determining generating user notifications are described in greater detail in U.S. patent application Ser. No. 14/174,487, which is incorporated by reference.

Additionally, the pump control module 602 may implement or otherwise execute a data prediction application 614 that calculates or otherwise determines one or more predicted values for the physiological condition sensed by the sensing arrangement 504 based on the sequence of the most recent measurement values received from the sensing arrangement 504. For example, the data prediction application 614 may calculate a predicted value for the user's glucose level at a particular amount of time in the future based on the recent measurement values received from the sensing arrangement 504 and/or the recent dosage commands generated by the command generation application 610. In some embodiments, the predicted value may be utilized by the particular operating mode being implemented by the command generation application 610 to modify current and/or future dosage commands (e.g., to suspend and/or resume infusion, increase and/or decrease the amount of fluid being delivered, or the like). Additionally, the predicted value may be utilized by the notification application 612 to generate notifications in accordance with the patient-specific notification criteria stored in the user settings registers 622. Various implementation details pertaining to determining predicted values and generating corresponding notifications are described in greater detail in U.S. patent application Ser. No. 14/261,266, which is incorporated by reference.

The illustrated pump control module 602 also implements or otherwise executes a diagnostics application 616 that determines the viability of a particular operating mode implemented by the command generation application 610. For example, in various operating modes may require a particular amount of historical delivery data, measurement data, calibration data, or the like in order to calculate control parameters for implementing the operating mode. Thus, prior to when an operating mode is to be entered, the diagnostics application 616 may perform one or more diagnostic checks to verify or otherwise confirm the required information is available for calculating the required control parameter(s) for implementing a subsequent instance of the operating mode. Various implementation details pertaining to operating mode diagnostics are described in greater detail in U.S. patent application Ser. No. 14/561,128, which is incorporated by reference.

Still referring to FIG. 6, the control parameter registers 620 generally represent the hardware, circuitry and/or other components of the pump control system 600 that are configured to store the pharmacokinetic control parameters or other control information for the control schemes, notification schemes, and/or operating modes implemented by the pump control module 602. When the command generation application 610 implements closed-loop PID control, the parameter registers 620 store the control parameters for the PID control, such as, for example, the target value for the physiological condition being regulated, the proportional gain coefficient, the integration gain coefficient, the derivative gain coefficient, and the like. Other control parameters that are influenced or otherwise dictated by the pharmacokinetics of the fluid being delivered may also be stored or maintained in the parameter registers 620. In various embodiments, the parameter registers 620 may store or maintain the prediction time for the data prediction application 614 and/or other parameter values utilized by the data prediction application 614 for calculating the predicted value at the prediction timeframe into the future (e.g., the number of recent measurement samples to utilize, weighting coefficients for the measurement samples, and the like). The parameter registers 620 may also store or maintain diagnostics criteria referenced by the diagnostics application 616 for the diagnostic checks (e.g., a minimum required amount of historical delivery data, measurement data, calibration data, or the like), which may be specific to the particular type of fluid being infused.

The user settings registers 622 generally represent the hardware, circuitry and/or other components of the pump control system 600 that are configured to store patient-specific parameters or other patient-specific information for the control schemes, notification schemes, and/or operating modes implemented by the pump control module 602. For example, the user setting registers 622 may store or maintain patient-specific control parameters and/or other control information referenced by the command generation application 610 when implementing a particular control scheme, such as insulin delivery limits for the patient, a patient-specific total daily insulin value, a patient-specific insulin sensitivity value, a patient-specific carbohydrate ratio value, patient-specific delivery thresholds, and/or other patient-specific mathematical model parameter values that characterize or otherwise describe the user's insulin sensitivity and/or meal response. Additionally, the user setting registers 622 may store or maintain patient-specific notification criteria, and/or other information referenced by the user notification application 612 for generating alerts or other notifications.

It should be understood that FIG. 6 is a simplified representation of a pump control system 600 for purposes of explanation and is not intended to limit the subject matter described herein in any way. For example, in some embodiments, the features and/or functionality of the motor control module 512 may be implemented by or otherwise integrated into the pump control system 600 and/or the pump control module 602, for example, by the command generation application 610 converting the dosage command into a corresponding motor command, in which case, the separate motor control module 512 may be absent from an embodiment of the infusion device 502. While FIG. 6 depicts the parameter registers 620 and the user settings registers 622 as being integrated with or into the memory 606, in various embodiments, either or both of the parameter registers 620 and the user settings registers 622 may be distinct or otherwise separate from memory 606, and the parameter registers 620 and the user settings registers 622 may be integrated with one another separate from the memory 606. In some embodiments, either or both of the parameter registers 620 and the user settings registers 622 are integrated with or into the pump control module 602, with the parameter values utilized by the control applications 610, 612, 614, 616 being loaded from the memory 606 to the registers 620, 622 of the pump control module 602 in response to identifying the particular type of fluid onboard the infusion device 200, 502, as described below.

Figure 7:
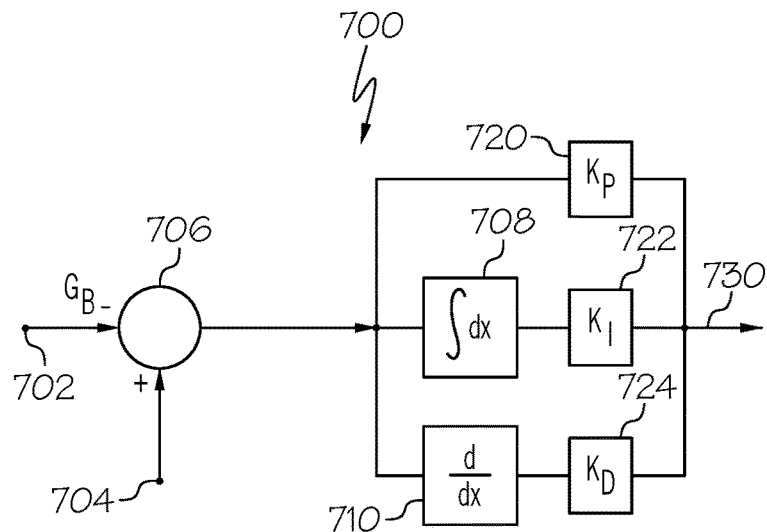
FIG. 7 is a block diagram of a closed-loop control system that may be implemented or otherwise supported by the pump control system in the fluid infusion device of FIG. 5 in one or more exemplary embodiments.

FIG. 7 depicts an exemplary closed-loop control system 700 that may be implemented by a pump control system 520, 600 (e.g., by the command generation application 610 implemented by the pump control module 602) to regulate a condition in the body of a user to a desired (or target) value in a closed-loop operating mode. It should be appreciated that FIG. 7 is a simplified representation of the closed-loop control system 700 for purposes of explanation and is not intended to limit the subject matter described herein in any way.

The illustrated closed-loop control system 700 receives or otherwise obtains a target glucose value at input 702. In exemplary embodiments, the target glucose value is stored or otherwise maintained by the infusion device 502 (e.g., in memory 606), however, in some alternative embodiments, the target value may be received from an external component (e.g., CCD 106 and/or computer 108). In one or more embodiments, the target glucose value may be dynamically calculated or otherwise determined prior to entering the closed-loop operating mode based on one or more patient-specific control parameters maintained in memory 606 (e.g., in registers 620, 622). For example, the target blood glucose value may be calculated based at least in part on a patient-specific reference basal rate and a patient-specific daily insulin requirement, which may be manually input by a user or dynamically determined based on historical delivery information over a preceding interval of time (e.g., the amount of insulin delivered over the preceding 24 hours). The closed-loop control system 700 also receives or otherwise obtains a current glucose measurement value from the sensing arrangement 504 at input 704. The illustrated closed-loop control system 700 implements or otherwise provides proportional-integral-derivative (PID) control to determine or otherwise generate dosage (or delivery) commands for operating the motor 510 based at least in part on the difference between the target glucose value and the current glucose measurement value. In this regard, the PID control attempts to minimize the difference between the measured value and the target value, and thereby regulates the measured value to the desired value. PID control parameters are applied to the difference between the target glucose level at input 702 and the measured glucose level at input 704 to generate or otherwise determine a dosage command provided at output 730. Based on that delivery command, the motor control module 512 operates the motor 510 to deliver the corresponding amount of onboard fluid to the body of the user to influence the user's glucose level, and thereby reduce the difference between a subsequently measured glucose level and the target glucose level.

The illustrated closed-loop control system 700 includes or otherwise implements a summation block 706 configured to determine a difference between the target value obtained at input 702 and the measured value obtained from the sensing arrangement 504 at input 704, for example, by subtracting the target value from the measured value. The output of the summation block 706 represents the difference between the measured and target values, which is then provided to each of a proportional term path, an integral term path, and a derivative term path. The proportional term path includes a gain block 720 that multiplies the difference by a proportional gain coefficient, $K_P$, to obtain the proportional term. The integral term path includes an integration block 708 that integrates the difference and a gain block 722 that multiplies the integrated difference by an integral gain coefficient, $K_I$, to obtain the integral term. The derivative term path includes a derivative block 710 that determines the derivative of the difference and a gain block 724 that multiplies the derivative of the difference by a derivative gain coefficient, $K_D$, to obtain the derivative term. The proportional term, the integral term, and the derivative term are then added or otherwise combined to obtain a delivery command that is utilized to operate the motor at output 730. Various implementation details pertaining to closed-loop PID control and determine gain coefficients are described in greater detail in U.S. Pat. No. 7,402,153, which is incorporated by reference.

In exemplary embodiments, the PID gain coefficients may be maintained by the memory 606 accessible to the pump control module 602. For example, the values for the gain coefficient blocks 720, 722, 724 may be maintained in the control parameter registers 620 and retrieved by the command generation application 610 during implementation of the closed-loop operating mode. In some embodiments, the PID gain coefficients are patient-specific and dynamically calculated or otherwise adjusted prior to entering the closed-loop operating mode based on one or more patient-specific control parameters maintained in the user settings registers 622 (e.g., an insulin sensitivity factor, a daily insulin requirement, an insulin limit, a reference basal rate, a reference fasting glucose, an active insulin action duration, pharmodynamical time constants, or the like) to compensate, correct, or otherwise adjust the PID gain coefficients to account for various operating conditions experienced and/or exhibited by the infusion device 502. Additionally, the target glucose value may be maintained in the user settings register 622 and retrieved by the command generation application 610 during operation.

Still referring to FIG. 7 with reference to FIGS. 1-6, in exemplary embodiments, the pump control system 520, 600 is configured to support regulating the physiological condition of the user using the closed-loop control system 700 with different types of fluid (e.g., different drugs) having different pharmacokinetics characteristics. For example, each fluid type from among a plurality of different possible fluid types may be associated with its own unique set of control parameters that reflect its unique pharmacokinetics characteristics. In one or more embodiments, the unique set of control parameters associated with a particular fluid type are transferred or otherwise loaded from the memory 606 into the registers 620, 622 referenced by the command generation application 610 when implementing the closed-loop control system 700. In other embodiments, the unique set of control parameters associated with a particular fluid type are downloaded or otherwise obtained from a remote server or another device 106, 108 within the infusion system 100 and transferred into the registers 620, 622 referenced by the command generation application 610 when implementing the closed-loop control system 700. In yet other embodiments, the memory 606 may store or otherwise maintain a reference set of control parameters which are converted or otherwise utilized to derive a unique set of control parameters associated with a particular fluid type. For example, the pump control module 602 may obtain pharmacokinetics information associated with the particular type of fluid currently in the reservoir 205, then utilize the relationship between the pharmacokinetics information associated with the identified fluid type and reference pharmacokinetics information associated with the reference set of control parameters to convert reference set of control parameters into updated values suitable for use with the identified fluid type (e.g., by scaling the reference set of control parameters up or down).

As described in greater detail below in the context of FIG. 8, the pump control system 520, 600 may initially operate the infusion device 502 to regulate a glucose level in the patient's body 501 using the closed-loop control system 700 with an initial type of insulin drug in the reservoir 205. Thus, the control parameter values reflecting the pharmacokinetics of the initial insulin drug and other patient-specific parameter values associated with the initial insulin drug are loaded into the registers 620, 622 and referenced by the command generation application 610 to regulate the user's glucose level using the initial insulin drug in accordance with the closed-loop operating mode. Thereafter, when the reservoir 205 becomes depleted, the reservoir 205 may be replaced with a new reservoir 205 containing a different type of insulin drug, or the reservoir 205 may be refilled with a different type of insulin drug. In response to identifying the different type of insulin drug onboard the infusion device 200, 502 having different pharmacokinetics than the initial insulin drug, the pump control module 602 automatically obtains the control parameter values reflecting the pharmacokinetics of the new insulin drug and other patient-specific parameter values associated with the new insulin drug and loads the obtained parameter values associated with the new insulin drug into the registers 620, 622. Thereafter, when implementing the closed-loop control system 700, the command generation application 610 references those updated pharmacokinetic and patient-specific control parameter values in the registers 620, 622 to regulate the user's glucose level in accordance with the closed-loop operating mode using the new insulin drug.

In a similar manner, the notification schemes implemented by the notification application 612, the prediction schemes implemented by the data prediction application 614, and the diagnostic checks implemented by the diagnostics application 616 may be updated to reflect the different pharmacokinetics of the different types of fluid that may be supported by the infusion device 502. For example, the notification criteria in the user settings registers 622 may be updated to reflect notification criteria that were previously specified by a user for the new insulin drug, or the notification criteria in the user settings registers 622 may be adjusted to reflect the different pharmacokinetics for the new insulin drug. In this regard, the patient may receive alerts relatively sooner or later to account for the faster or slower response of the glucose level in the patient's body to dosages of the new insulin drug. Similarly, the prediction time, the number of samples, the weighting factors, and other control parameters for the data prediction algorithm utilized by the data prediction application 614 may be adjusted to reflect the different pharmacokinetics for the new insulin drug. For example, the prediction time may be reduced and/or the most recent measurement samples may be more heavily weighted to account for a new insulin drug with a faster response time in the body, or conversely, the prediction time may be increased to account for a new insulin drug with a slower response time in the body. Likewise, the diagnostics criteria referenced by the diagnostics application 616 for the diagnostic checks may be changed to reflect different amounts of historical delivery data, measurement data, calibration data, or the like that may be required (e.g., by regulatory requirements) for implementing a particular operating mode with a particular drug type.

Additionally, it should be noted that the subject matter described herein is not limited to the closed-loop operating mode depicted in FIG. 7, and other operating modes supported by the command generation application 610 may also be updated in an equivalent manner to support different types of fluids being infused. For example, the basal infusion rate and/or the predictive suspend threshold utilized by a PLGM operating mode of the command generation application 610 may be updated to reflect the faster or slower action of the particular type of insulin drug being delivered. Similarly, the basal infusion rate and/or the suspend threshold utilized by a LGS operating mode of the command generation application 610 and the open-loop basal infusion rate utilized by an open-loop operating mode of the command generation application 610 may be updated to reflect the different pharmacokinetics of the particular type of insulin drug being delivered. In this regard, upon a different type of fluid being infused by the infusion device 502, all of the control parameters utilized by the respective operating modes or applications 610, 612, 614, 616 supported by the pump control module 602 that are dictated by or otherwise chosen based on the pharmacokinetics characteristics of the fluid being infused may be updated across the board to support subsequent operation of the infusion device 502.

Figure 8:
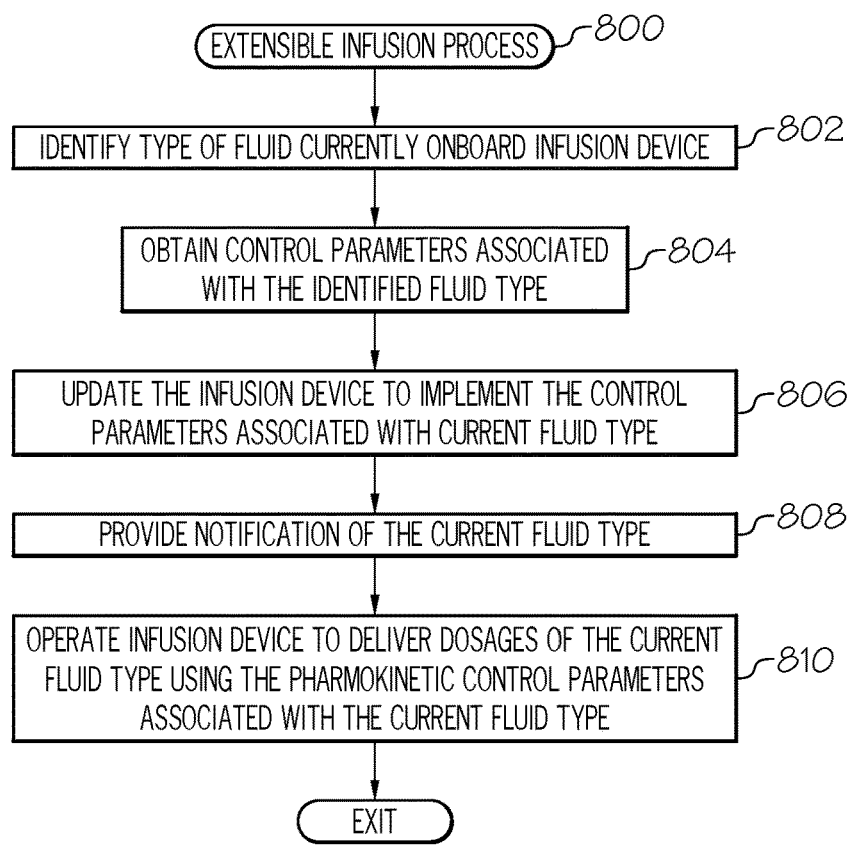
FIG. 8 is a flow diagram of an exemplary extensible infusion process suitable for use with the control system of FIG. 5.

FIG. 8 depicts an exemplary extensible infusion process 800 suitable for implementation by a control system associated with a fluid infusion device to adjust or otherwise adapt its operations to accommodate different infused fluids having different pharmacokinetics characteristics. For purposes of explanation, the extensible infusion process 800 may be described herein in the context of a closed-loop operating mode, however, it will be appreciated that the subject matter described herein is not limited to the particular operating mode being implemented. Various tasks performed in connection with the extensible infusion process 800 may be performed by hardware, firmware, software executed by processing circuitry, or any combination thereof. For illustrative purposes, the following description refers to elements mentioned above in connection with FIGS. 1-7. In practice, portions of the extensible infusion process 800 may be performed by different elements of the control system 500, such as, for example, the infusion device 502, the pump control system 520, 600, the pump control module 602, the communications interface 604, the memory 606, the user interface 540, 608, the command generation application 610, the notification application 612, the data prediction application 614, the diagnostics application 616 and/or the user interface 540, 608. It should be appreciated that the extensible infusion process 800 may include any number of additional or alternative tasks, the tasks need not be performed in the illustrated order and/or the tasks may be performed concurrently, and/or the extensible infusion process 800 may be incorporated into a more comprehensive procedure or process having additional functionality not described in detail herein. Moreover, one or more of the tasks shown and described in the context of FIG. 8 could be omitted from a practical embodiment of the extensible infusion process 800 as long as the intended overall functionality remains intact.

In exemplary embodiments, the extensible infusion process 800 initializes or otherwise begins by detecting or otherwise identifying the type of fluid that is currently onboard the infusion device (task 802). In this regard, the pump control system 520, 600 identifies or otherwise determines when the type of fluid within the reservoir 205 is different from the type of fluid that was previously onboard the infusion device 200, 502. In some embodiments, when a new reservoir 205 is inserted into the infusion device 200, 502 or when the reservoir 205 is refilled, the pump control module 602 may generate or otherwise provide a graphical user interface (GUI) on the user interface 540, 608 associated with the infusion device 200, 502 that prompts a user to identify or otherwise confirm the type of insulin drug within the reservoir 205, with the pump control module 602 identifying the type of fluid onboard the infusion device 200, 502 based on the user input received via the GUI. For example, in response to insertion of a reservoir 205 into the infusion device 200, 502, the pump control module 602 may automatically generate or otherwise provide a GUI on the user interface 540, 608 that includes a list of the possible types of insulin drugs that are supported by the pump control system 520, 602 and identify the type of fluid onboard the infusion device 200, 502 based on the user selection from the list. In such embodiments, the pump control module 602 may store or otherwise maintain, in memory 606, one or more data tables that maintain information identifying the different types of insulin drugs supported by the pump control system 520, 600 and corresponding sets of control parameters associated with the respective insulin drug types. For example, each entry or row in a data table in memory 606 may correspond to a particular insulin drug type, with the columns of that respective entry or row including values for the pharmacokinetics control parameters or other pharmacokinetics information associated with that particular insulin drug type along with patient-specific values or criteria for that particular insulin drug type.

In one or more embodiments, the pump control system 520, 600 automatically detects the type of insulin infusion drug onboard the infusion device 200, 502 based on a detectable feature or characteristic (or a combination of detectable features) of the reservoir 205. For example, the reservoir 205 may include a particular physical feature (e.g., a tab, a notch, a physical pattern, or the like) or a combination thereof that is uniquely associated with a particular infusion drug type (e.g., only vials or reservoirs of that drug include the particular feature), with the infusion device 200, 502 including one or more contact sensors configured to detect the presence or absence of the particular physical features of the reservoirs 205 associated with the possible infusion drug types supported by the pump control system 520, 600. In such embodiments, the pump control module 602 may be coupled to the output of the contact sensor(s) and detect or otherwise identify the type of insulin infusion drug onboard the infusion device 200, 502 based on the output of the contact sensor(s).

Similarly, the reservoir 205 may include a particular optical, electrical, or magnetic feature that is uniquely associated with a particular infusion drug type, with the infusion device 200, 502 including corresponding sensors configured to detect the presence or absence of the particular features of the reservoir 205 onboard the infusion device 200, 502. For example, the reservoir 205 may include a barcode or similar feature imprinted or provided thereon that is scanned or otherwise read by an appropriate optical sensing device, with the pump control module 602 utilizing the scanned identifier to identify the type of insulin drug in the reservoir 205 onboard the infusion device 200, 502. In this regard, in some embodiments, using the barcode or other scanned identifier obtained from the reservoir 205, the pump control module 602 may operate the communications interface 604 to transmit or otherwise provide an identification request to a remote server (or another device 106, 108 in an infusion system 100), which in turn, performs a look-up operation using the scanned identifier included in the request to identify the insulin drug type and provide a corresponding response to the pump control module 602. For example, the remote server may provide, to the pump control module 602, the name or other identifier associated with the insulin drug type currently onboard the infusion device 200, 502 along with the pharmacokinetics characteristics associated with that insulin drug type.

Referring again to FIG. 8, after identifying the type of drug onboard the infusion device, the extensible infusion process 800 continues by obtaining a unique set of control parameters associated with the identified drug type (task 804). As described above, the unique set of control parameters associated with a particular drug type includes pharmacokinetics control parameters that reflect or are otherwise dictated by the unique pharmacokinetics characteristics of that particular drug type and utilized by the command generation application 610, and potentially other applications 612, 614, 616, implemented by the pump control module 602 to deliver the fluid to the patient. Additionally, the unique set of control parameters associated with a particular drug type includes patient-specific parameters, criteria, or settings that are utilized by the applications 610, 612, 614, 616 to adjust or otherwise modify operations of the pump control module 602 in a personalized or patient-specific manner.

In one or more exemplary embodiments, the unique set of control parameters for the identified drug type currently onboard the infusion device 200, 502 are stored or otherwise maintained onboard the infusion device 200, 502 in memory 606 and retrieved or otherwise obtained from memory 606. For example, the pump control module 602 may access the data table(s) in memory 606 that maintain information for the possible insulin drugs supported by the pump control system 520, 600 and perform a lookup operation using an identifier associated with the identified onboard drug type to locate a corresponding entry associated with the identified onboard drug type that includes values for the pharmacokinetics control parameters, patient-specific criteria or settings, and/or other pharmacokinetics information associated with the onboard insulin drug type.

In another embodiment, the unique set of control parameters for the identified drug type currently onboard the infusion device 200, 502 are downloaded, retrieved or otherwise obtained from an external device. For example, the pump control module 602 may operate the communications interface 604 to transmit or otherwise provide a request for the set of control parameters for the identified drug type to another device 106, 108 in the infusion system 100. In response to receiving a request from the pump control module 602, the requested device 106, 108 may contact a remote server, a networked database, or the like via an external communications network (e.g., the Internet, a cellular network, or the like) to download or otherwise obtain the requested set of control parameters for the identified drug type. Thereafter, the requested device 106, 108 relays or otherwise retransmits the downloaded set of control parameters for the identified drug type to the pump control module 602. In some embodiments, the pump control module 602 may contact a remote server, a networked database, or the like via an external communications network directly without using another device 106, 108 of the infusion system 100 as an intermediary. For example, the pump control module 602 may transmit a download request identifying the currently onboard insulin drug type to a remote server, which, in turn, responds by providing the set of control parameters for the identified drug type to the pump control module 602. In some embodiments, the pump control module 602 may update the memory 606 to persistently maintain the downloaded set of control parameters for future reference, for example, by creating a new entry or row in one or more data tables in memory 606 that stores or otherwise maintains the downloaded parameter values in association with the identified insulin drug type currently onboard.

In yet other embodiments, the pump control module 602 calculates or otherwise determines the unique set of control parameters for the identified drug type currently onboard the infusion device 200, 502 by converting a reference set of control parameters based on the pharmacokinetics characteristics of the identified drug type, as described in greater detail below in the context of FIG. 9. For example, the memory 606 may store a reference set of control parameters associated with a particular insulin drug type, which are then converted to different values for different insulin drug types based on the relationship between pharmacokinetics characteristics of the identified insulin drug type currently onboard the infusion device 200, 502 with respect to the pharmacokinetics characteristics of the reference insulin drug type. In this regard, the ratio between the value for a particular pharmacokinetics characteristic of the onboard insulin drug type to the value of that pharmacokinetics characteristic associated with the reference insulin drug type may be used to scale a reference value for a pharmacokinetics control parameter up or down to an updated value that reflects the change in pharmacokinetics characteristics associated with using the onboard insulin drug type rather than the reference insulin drug type. Depending on the embodiment, the pharmacokinetics characteristics of the identified insulin drug type currently onboard the infusion device 200, 502 used in the conversion may be stored local to the infusion device 200, 502 in memory 606, or alternatively, the pump control module 602 may download the pharmacokinetics characteristics from an external device in a similar manner as described above.

It should be noted that the unique set of control parameters for the identified drug type currently onboard the infusion device 200, 502 may be obtained in a variety of manners. For example, the pump control module 602 may construct the unique set of control parameters by downloading the pharmacokinetics control parameters for the onboard insulin drug type from an external device while converting patient-specific control parameters for a reference drug type (e.g., the preceding onboard insulin drug type) to updated values using pharmacokinetics characteristics associated with the current onboard insulin drug type, which may also be downloaded from the external device in concert with downloading the pharmacokinetics control parameters. As another example, the pump control module 602 may construct the unique set of control parameters by converting pharmacokinetics control parameters for a reference drug type to updated values using pharmacokinetics characteristics associated with the current onboard insulin drug type while maintaining the same patient-specific control parameters for the reference drug type for use with the current onboard insulin drug type.

Still referring to FIG. 8, after obtaining the set of control parameters associated with the currently onboard drug type, the extensible infusion process 800 continues by updating the infusion device to utilize or otherwise implement that unique set of control parameters during subsequent autonomous operation of the infusion device (task 806). In this regard, the pump control module 602 transfers or otherwise loads the unique set of control parameters associated with the onboard drug type into the registers 620, 622 referenced by the applications 610, 612, 614, 616 that control operation of the infusion device 200, 502. For the illustrated embodiment of FIG. 6, the values for the pharmacokinetics control parameters associated with the current insulin drug type are transferred to their corresponding control parameter registers 620, and similarly, the values for the patient-specific control parameters associated with the current insulin drug type are transferred to the corresponding user settings registers 622.

In the illustrated embodiment, the extensible infusion process 800 generates or otherwise provides a user notification that indicates the currently onboard fluid type and automatically operates the infusion device in accordance with the unique set of control parameters associated with currently onboard fluid type (tasks 808, 810). For example, the pump control module 602 may generate an icon, a modal window, a textual notification, or another suitable graphical element on a display device 540, 608 associated with the infusion device 502 that indicates, to the user, the fluid type that has been identified by the pump control module 602 as being currently onboard and whose control parameters will be utilized to control operations of the infusion device 502. Thereafter, the pump control module 602 may autonomously operate the motor 507 in accordance with the control parameters associated with currently onboard fluid type to deliver dosages of the fluid to the body 501 of the patient. For example, as described above, the closed-loop operating mode implemented by the command generation application 610 may utilize the unique PID gain coefficients associated with the currently onboard fluid type that have been transferred to the control parameter registers 620 to implement the closed-loop control system 700 and deliver dosages configured to regulate the patient's glucose level to a target value. Additionally, the pump control module 602 utilizes control parameters associated with currently onboard fluid type to automatically generate appropriate user notifications, perform diagnostic checks, data predictions, and the like.

It should be noted that the extensible infusion process 800 may be automatically initiated by the pump control system 520, 600 whenever a new reservoir 205 is inserted in the infusion device 200, 502 (or alternatively, whenever the reservoir cap 223 is reengaged with the housing 202 after the reservoir 205 is refilled). In this regard, prior to an iteration of the extensible infusion process 800, the pump control module 602 may automatically operate the motor 507 to deliver dosages of an initial insulin drug type to regulate a glucose level in the patient's body 501 in accordance with the operating modes or control schemes implemented by the applications 610, 612, 614, 616 and the unique set of control parameters associated with that initial insulin drug type that are maintained in the control parameter registers 620, 622. Thereafter, when a new reservoir 205 with a different insulin drug is inserted into the housing 202, the pump control module 602 may automatically obtain unique set of control parameters associated with the new insulin drug, update the control parameter registers 620, 622 by transferring those obtained control parameter values to the control parameter registers 620, 622, and thereafter automatically operate the motor 507 to deliver dosages of a new insulin drug type to regulate the glucose level in the patient's body 501 in accordance with the unique set of control parameters associated with new insulin drug type. In this regard, the pump control module 602 autonomously controls operation of the infusion device 200, 502 using the same operating modes, control schemes and/or algorithms that were utilized by the applications 610, 612, 614, 616 for the preceding insulin drug type, but with different control parameters that reflect the different pharmacokinetics characteristics of the new insulin drug type. If another reservoir 205 containing that initial insulin drug type is subsequently inserted into the infusion device 200, 502, the pump control module 602 may automatically perform another iteration of the extensible infusion process 800 to transfer the prior control parameters that reflect the pharmacokinetics characteristics of the initial insulin drug type back into the control parameter registers 620, 622 for subsequent autonomous operation. In this manner, the pump control system 520, 600 is dynamically extensible to accommodate whichever type of fluid is provided in the reservoir 205.

Figure 9:
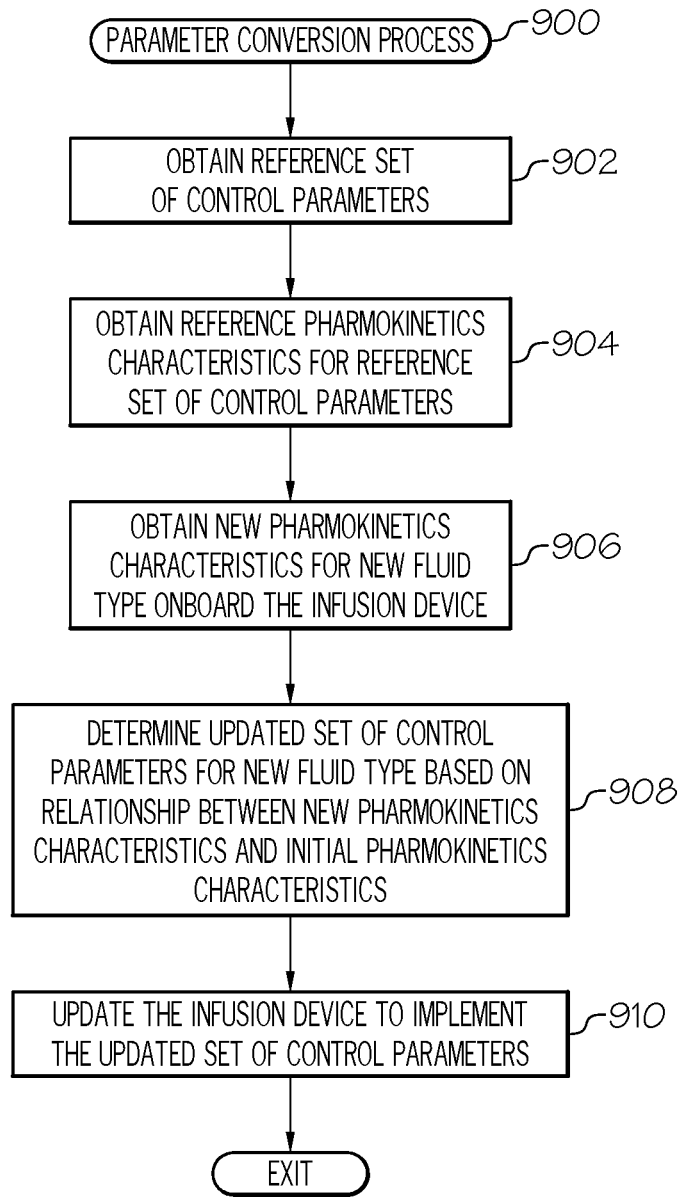
FIG. 9 is a flow diagram of an exemplary parameter conversion process suitable for use with the extensible infusion process of FIG. 8 in one or more exemplary embodiments.

FIG. 9 depicts an exemplary parameter conversion process 900 suitable for implementation with an extensible infusion process 800 to accommodate different infused fluids having different pharmacokinetics characteristics. Various tasks performed in connection with the parameter conversion process 900 may be performed by hardware, firmware, software executed by processing circuitry, or any combination thereof. For illustrative purposes, the following description refers to elements mentioned above in connection with FIGS. 1-7. In practice, portions of the parameter conversion process 900 may be performed by different elements of the control system 500, such as, for example, the infusion device 502, the pump control system 520, 600, the pump control module 602, the communications interface 604, the command generation application 610, the notification application 612, the data prediction application 614, the diagnostics application 616 and/or the user interface 540, 608. It should be appreciated that the parameter conversion process 900 may include any number of additional or alternative tasks, the tasks need not be performed in the illustrated order and/or the tasks may be performed concurrently, and/or the parameter conversion process 900 may be incorporated into a more comprehensive procedure or process having additional functionality not described in detail herein. Moreover, one or more of the tasks shown and described in the context of FIG. 9 could be omitted from a practical embodiment of the parameter conversion process 900 as long as the intended overall functionality remains intact.

The parameter conversion process 900 begins by retrieving or otherwise obtaining a reference set of control parameters for operating the infusion device and corresponding reference pharmacokinetics characteristics associated with the reference set of control parameters (tasks 902, 904). The reference set of control parameters may correspond to a particular fluid type supported by the pump control system 520, 600. For example, the reference set of control parameters may be associated with an insulin drug type for which the operating modes, control schemes, and the like implemented by the pump control module 602 were initially designed for use with. In this regard, the reference set of control parameters may be dictated or otherwise influenced by the pharmacokinetics characteristics of that insulin drug type. In some embodiments, the reference set of control parameters and reference pharmacokinetics characteristics of the reference insulin drug type are stored or otherwise maintained in memory 606. In other embodiments, the reference set of control parameters and reference pharmacokinetics characteristics of the reference insulin drug type may be downloaded or otherwise obtained by the pump control module 602 from a remote device. In yet other embodiments, the reference set of control parameters and reference pharmacokinetics characteristics may correspond to the preceding infusion drug type that was being delivered by the infusion device 200, 502 prior to the reservoir 205 being replaced or refilled.

The parameter conversion process 900 continues by retrieving or otherwise obtaining pharmacokinetics characteristics that reflect the typical biological response to the new insulin drug type onboard the infusion device (task 906). Depending on the embodiment, the pharmacokinetics characteristics of the new insulin drug type (alternatively referred to herein as the new pharmacokinetics characteristics) may be stored or otherwise maintained in memory 606, or alternatively, the new pharmacokinetics characteristics associated with the new insulin drug type may be downloaded or otherwise obtained by the pump control module 602 from a remote device. After obtaining the new pharmacokinetics characteristics, the parameter conversion process 900 calculates or otherwise determines an updated set of control parameters for operating the infusion device to deliver the new insulin drug type based on the relationship between the reference pharmacokinetics characteristics and the new pharmacokinetics characteristics (task 908). In this regard, the pump control module 602 may ratiometrically increase or decrease values from the reference set of control parameters based on the ratio of the corresponding new pharmacokinetics characteristics that influence a respective control parameter to the counterpart reference pharmacokinetics characteristics that influence that control parameter. Thus, the closed-loop PID gain coefficient values may be adjusted so that the closed-loop PID control system 700 responds faster after identifying a faster acting insulin onboard the infusion device 502, or alternatively, slower after identifying a slower acting insulin onboard.

Thereafter, the parameter conversion process 900 updates the infusion device to implement the updated set of control parameters with the preexisting operating modes, control schemes, and the like that are supported by the infusion device (task 910). As described above, the values for the updated set of control parameters may be transferred to the parameter registers 620, 622 referenced by the control applications 610, 612, 614, 616 during autonomous operation of the infusion device 200, 502. For example, values for the updated set of control parameters may be used to overwrite the corresponding values for the reference set of control parameters that were previously transferred or maintained in the parameter registers 620, 622. Thereafter, the pump control module 602 autonomously generates dosage commands, provides user notifications, performs diagnostics checks, and the like in accordance with the new values from the updated set of control parameters in the registers 620, 622 during subsequent operation of the infusion device 200, 502.

To briefly summarize, the subject matter describes herein provides an extensible infusion device that can accommodate multiple different types of fluid for infusion. In this regard, control schemes or algorithms that have been tested, verified, certified, or otherwise approved for use (e.g., by regulatory bodies or the like) may be extended to be used with new drugs that are developed during the lifetime of the infusion device. For example, values for gain coefficients of a PID control system may be automatically updated to values that reflect the pharmacokinetics of a new drug, with the PID control system autonomously operating the infusion device by generating dosage commands to deliver the new drug to regulate a physiological condition of the user to a target value using the same PID control-loop that was utilized for a previous drug but with the updated gain coefficient values associated with the new drug. Similarly, values for patient-specific parameters may be updated to reflect values that have either been specified by a user for use with the new drug, or alternatively, patient-specific parameters may be adjusted to reflect the pharmacokinetics of the new drug. The updated patient-specific parameter values may then be utilized to adjust pharmacokinetic control parameters (e.g., PID gain coefficient values) in a patient-specific manner to fine tune dosage commands for the patient, or the updated patient-specific parameter values may be utilized to modify the notification behavior of the infusion device (e.g., based on updated patient-specific notification criteria) in a manner that accounts for the pharmacokinetics of the new drug. Predictive operations, diagnostics operations, or other behaviors of the infusion device may also adapt to account for the pharmacokinetics of whatever drug is currently onboard.

For the sake of brevity, conventional techniques related to glucose sensing and/or monitoring, closed-loop glucose control, predictive glucose management, sensor calibration and/or compensation, and other functional aspects of the subject matter may not be described in detail herein. In addition, certain terminology may also be used in the herein for the purpose of reference only, and thus is not intended to be limiting. For example, terms such as "first", "second", and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. At least one non-transitory computer readable medium having stored thereon instructions that are configurable to cause at least one processor to perform a method comprising:
    operating a medical device to deliver a fluid to a body of a user in accordance with an operating mode using initial values for control parameters of the operating mode, wherein the fluid influences a physiological condition of the user;
    identifying a different fluid type associated with the fluid from among a plurality of possible fluid types, the different fluid type having pharmacokinetics characteristics different from a previous fluid type;
    in response to identifying the different fluid type, updating the initial values for the control parameters to updated values different from the initial values and the updated values reflecting the pharmacokinetics characteristics of the different fluid type, wherein the updated values comprise an updated gain coefficient value for a closed-loop operating mode; and
    thereafter operating the medical device in accordance with the operating mode using the updated values for the control parameters of the operating mode by generating dosage commands to deliver the fluid to regulate the physiological condition of the user to a target value using the updated gain coefficient value.

2. The at least one non-transitory computer readable medium of claim 1, wherein the method further comprises generating a list of the plurality of possible fluid types at a user interface and identifying the different fluid type in response to user selection of the different fluid type from the list.

3. The at least one non-transitory computer readable medium of claim 1, wherein identifying the different fluid type comprises identifying the different fluid type based on a feature of a reservoir inserted into a housing of the medical device detected by a sensing arrangement.

4. The at least one non-transitory computer readable medium of claim 1, wherein the method further comprises downloading the pharmacokinetics characteristics associated with the different fluid type from another device via a communications interface and converting the initial values to the updated values based on a relationship between the pharmacokinetics characteristics associated with the different fluid type and initial pharmacokinetics characteristics associated with the previous fluid type.

5. The at least one non-transitory computer readable medium of claim 1, wherein:
the control parameters comprise gain coefficients for a closed-loop control system;
the initial values comprise first gain coefficient values;
the updated values comprise second gain coefficient values;
the at least one processor operates a motor to deliver the fluid using the initial values by generating a first command for operating the motor based on a first difference between a first measurement value for the physiological condition of the user and the target value for the physiological condition of the user using the first gain coefficient values; and
the at least one processor operates the motor to deliver the fluid using the updated values by generating a second command for operating the motor based on a second difference between a second measurement value for the physiological condition of the user and the target value for the physiological condition of the user using the second gain coefficient values.

6. The at least one non-transitory computer readable medium of claim 1, wherein:
the updated values comprise an updated value for a patient-specific parameter; and
the at least one processor operates a motor to deliver the fluid to the user in accordance with the operating mode using the updated values by generating the dosage commands to deliver the fluid in accordance with the operating mode in a manner that is influenced by the updated value.

7. The at least one non-transitory computer readable medium of claim 1, wherein:
the updated values comprise an updated prediction time reflecting the pharmacokinetics characteristics of the different fluid type; and
the at least one processor operates a motor to deliver the fluid to the user in accordance with the operating mode using the updated values by determining a predicted value for the physiological condition of the user corresponding to the updated prediction time into the future and automatically adjusting the dosage commands for delivering the fluid in accordance with the operating mode in a manner that is influenced by the predicted value.

8. The at least one non-transitory computer readable medium of claim 1, the updated values comprising an updated patient-specific notification threshold value, wherein the method further comprises automatically generating a user notification on a display device based on the updated patient-specific notification threshold value while operating a motor to deliver the fluid to the user in accordance with the operating mode.

9. The at least one non-transitory computer readable medium of claim 1, wherein the fluid comprises insulin.

10. The at least one non-transitory computer readable medium of claim 1, wherein the fluid comprises a medicament.

11. At least one non-transitory computer readable medium having stored thereon instructions that are configurable to cause at least one processor to perform a method comprising:
identifying a current fluid type from among a plurality of possible fluid types, the current fluid type having pharmacokinetics characteristics different from other fluid types of the plurality of possible fluid types;
in response to identifying the current fluid type, updating a control parameter maintained by a data storage element to an updated value reflecting the pharmacokinetics characteristics of the current fluid type, wherein the updated value comprises an updated patient-specific notification threshold value;
thereafter operating a medical device in accordance with an operating mode using the updated value for the control parameter of the operating mode; and
automatically generating a user notification on a display device based on the updated patient-specific notification threshold value while operating the medical device in accordance with the operating mode.

12. The at least one non-transitory computer readable medium of claim 11, wherein the method further comprises generating a list of the plurality of possible fluid types at a user interface and identifying the current fluid type in response to user selection of the current fluid type from the list.

13. The at least one non-transitory computer readable medium of claim 11, wherein identifying the current fluid type comprises identifying the current fluid type based on a feature of a reservoir inserted into a housing of the medical device detected by a sensing arrangement.

14. The at least one non-transitory computer readable medium of claim 11, wherein the method further comprises downloading the pharmacokinetics characteristics associated with the current fluid type from another device via a communications interface and converting an initial value for the control parameter to the updated value based on a relationship between the pharmacokinetics characteristics associated with the current fluid type and initial pharmacokinetics characteristics associated with a previous fluid type.

15. The at least one non-transitory computer readable medium of claim 11, wherein the medical device comprises an infusion device operable to deliver a fluid having the current fluid type to a body of a user, wherein the fluid influences a physiological condition of the user.

16. The at least one non-transitory computer readable medium of claim 15, wherein the infusion device comprises an insulin pump.

17. The at least one non-transitory computer readable medium of claim 15, wherein the infusion device comprises an injection pen.

18. At least one non-transitory computer readable medium having stored thereon instructions that are configurable to cause at least one processor to perform a method comprising:
identifying a current fluid type from among a plurality of possible fluid types, the current fluid type having pharmacokinetics characteristics different from other fluid types of the plurality of possible fluid types;
in response to identifying the current fluid type, updating a control parameter maintained by a data storage element to an updated value reflecting the pharmacokinetics characteristics of the current fluid type, wherein the updated value comprises an updated prediction time reflecting the pharmacokinetics characteristics of the current fluid type;

determining a predicted value for a physiological condition of a user corresponding to the updated prediction time into the future; and thereafter operating a medical device in accordance with an operating mode using the updated value for the control parameter of the operating mode in a manner that is influenced by the predicted value.

19. The at least one non-transitory computer readable medium of claim 18, wherein the medical device comprises an infusion device comprising a motor operable to deliver a fluid having the current fluid type to a body of the user in accordance with the operating mode using the predicted value, wherein the fluid influences the physiological condition of the user.

20. The at least one non-transitory computer readable medium of claim 18, wherein the method further comprises downloading the pharmacokinetics characteristics associated with the current fluid type from another device via a communications interface and converting an initial prediction time to the updated prediction time based on a relationship between the pharmacokinetics characteristics associated with the current fluid type and initial pharmacokinetics characteristics associated with a previous fluid type.

* * * * *